(12) United States Patent
Mao et al.

(10) Patent No.: US 11,540,754 B2
(45) Date of Patent: *Jan. 3, 2023

(54) USING NEAR AND FAR DETECTORS TO MEASURE OXYGEN SATURATION

(71) Applicant: ViOptix, Inc., Newark, CA (US)

(72) Inventors: Jimmy Jian-min Mao, Fremont, CA (US); Robert E. Lash, Redwood City, CA (US)

(73) Assignee: ViOptix, Inc., Newark, CA (US)

( * ) Notice: Subject to any disclaimer, the term of this patent is extended or adjusted under 35 U.S.C. 154(b) by 270 days.

This patent is subject to a terminal disclaimer.

(21) Appl. No.: 16/748,684

(22) Filed: Jan. 21, 2020

(65) Prior Publication Data
US 2020/0155051 A1    May 21, 2020

Related U.S. Application Data

(60) Continuation of application No. 15/485,171, filed on Apr. 11, 2017, now Pat. No. 10,537,271, which is a division of application No. 12/116,013, filed on May 6, 2008, now Pat. No. 9,622,694, which is a continuation-in-part of application No. 29/305,102, filed on Mar. 13, 2008, now Pat. No. Des. 587,375, and a continuation-in-part of application No.
(Continued)

(51) Int. Cl.
*A61B 5/1455* (2006.01)

(52) U.S. Cl.
CPC ...... *A61B 5/14552* (2013.01); *A61B 5/14553* (2013.01); *A61B 2562/0238* (2013.01); *A61B 2562/0242* (2013.01); *A61B 2562/043* (2013.01)

(58) Field of Classification Search
CPC ............... A61B 5/0059; A61B 5/0205; A61B 5/1455; A61B 5/14551; A61B 5/14552; A61B 5/14553; A61B 5/68; A61B 5/6803; A61B 5/6814; A61B 2562/0238; A61B 2562/0242; A61B 2562/043
See application file for complete search history.

(56) References Cited

U.S. PATENT DOCUMENTS

D321,761 S    11/1991   Shimizu
D327,325 S     6/1992   Strand
(Continued)

OTHER PUBLICATIONS

Tuchin, "Tissue Optics: Light Scattering Methods and Instruments for Medical Diagnosis", Tutorial Texts in Optical Engineering, vol. TT38, 2000, p. 18-33.
(Continued)

*Primary Examiner* — Chu Chuan Liu
(74) *Attorney, Agent, or Firm* — Aka Chan LLP

(57) ABSTRACT

A device includes source and detector sensors. In a specific implementation, the device has two near detectors, two far detectors, and two sources. The two near detectors are arranged closer to the two sources than the two far detectors. A light-diffusing layer covers the two near detectors. The device may be part of a medical device that is used to monitor or measure oxygen saturation levels in a tissue. In a specific implementation, light is transmitted into the tissue and received by the detectors. An attenuation coefficient is first calculated for a shallow layer of tissue. The attenuation coefficient is then used to calculate an attenuation coefficient for a deep layer of tissue.

25 Claims, 13 Drawing Sheets

Related U.S. Application Data

29/281,301, filed on Jun. 20, 2007, now Pat. No. Des. 568,479.

(56) References Cited

U.S. PATENT DOCUMENTS

| | | | |
|---|---|---|---|
| 5,139,025 A | 8/1992 | Lewis et al. | |
| 5,217,013 A | 6/1993 | Lewis et al. | |
| 5,429,128 A | 7/1995 | Cadell et al. | |
| 5,465,714 A | 11/1995 | Schening | |
| 5,477,853 A | 12/1995 | Farkas et al. | |
| 5,482,034 A | 1/1996 | Lewis et al. | |
| 5,490,506 A | 2/1996 | Takatani et al. | |
| 5,524,617 A | 6/1996 | Mannheimer | |
| 5,529,065 A * | 6/1996 | Tsuchiya | A61B 5/0059 600/310 |
| 5,584,296 A | 12/1996 | Cui et al. | |
| 5,697,367 A | 12/1997 | Lewis et al. | |
| 5,795,292 A | 8/1998 | Lewis et al. | |
| 5,797,841 A | 8/1998 | Delonzor et al. | |
| 5,839,439 A | 11/1998 | Nierlich et al. | |
| 5,902,235 A | 5/1999 | Lewis et al. | |
| 5,919,133 A | 7/1999 | Taylor et al. | |
| D425,203 S | 5/2000 | Sheehan et al. | |
| 6,353,226 B1 | 3/2002 | Khalil et al. | |
| 6,516,209 B2 | 2/2003 | Cheng et al. | |
| D471,281 S | 3/2003 | Baura et al. | |
| 6,587,703 B2 | 7/2003 | Cheng et al. | |
| 6,597,931 B1 | 7/2003 | Cheng et al. | |
| 6,615,065 B1 | 9/2003 | Barrett | |
| 6,662,030 B2 | 12/2003 | Khalil et al. | |
| 6,671,526 B1 | 12/2003 | Aoyagi et al. | |
| 6,735,458 B2 | 5/2004 | Cheng et al. | |
| 6,748,254 B2 | 6/2004 | O'Neill et al. | |
| D495,055 S | 8/2004 | Siber | |
| 7,072,701 B2 | 7/2006 | Chen et al. | |
| 7,247,142 B1 | 7/2007 | Elmandjra et al. | |
| 7,355,688 B2 | 4/2008 | Lash et al. | |
| 2002/0091335 A1 | 7/2002 | John et al. | |
| 2003/0023151 A1 | 1/2003 | Khalil et al. | |
| 2005/0268916 A1 | 12/2005 | Mumford et al. | |
| 2007/0038251 A1 | 2/2007 | Pachon et al. | |
| 2007/0148260 A1 | 6/2007 | Denault | |
| 2007/0203405 A1 * | 8/2007 | Shimomura | A61B 5/14532 600/316 |
| 2007/0208269 A1 | 9/2007 | Mumford et al. | |
| 2008/0015424 A1 | 1/2008 | Bemreuter | |

OTHER PUBLICATIONS

Taitelbaum et al., "Approximate Theory of Photon Migration in a Two-Layer Medium", Applied Optics, vol. 28, No. 12, Jun. 15, 1989, pp. 2245-2249.

Okada et al., "Theoretical and Experimental Investigation of Near-Infrared Light Propagation in a Model of the Adult Head", Applied Optics, vol. 36, No. 1, Jan. 1, 1997, pp. 21-31.

* cited by examiner

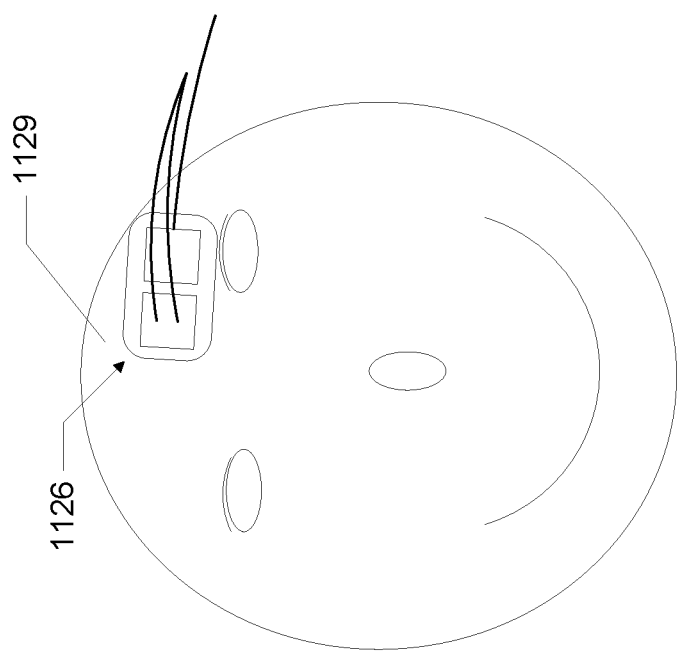
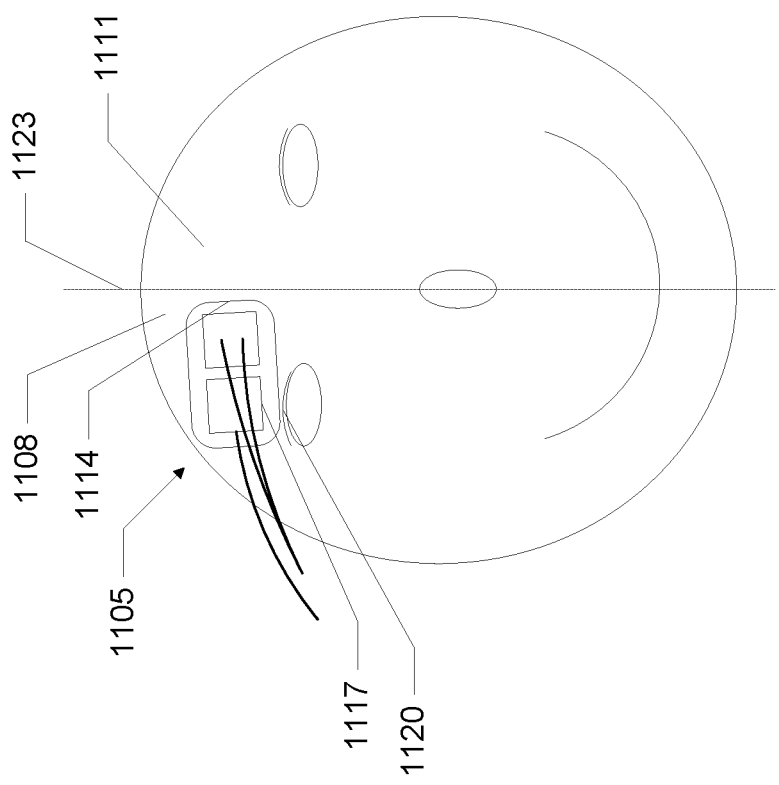
Figure 11a
Figure 11b

USING NEAR AND FAR DETECTORS TO MEASURE OXYGEN SATURATION

CROSS-REFERENCE TO RELATED APPLICATIONS

This patent application is a continuation of U.S. patent application Ser. No. 15/485,171, filed Apr. 11, 2017, issued as U.S. Pat. No. 10,537,271 on Jan. 21, 2020, which is a divisional of U.S. patent application Ser. No. 12/116,013, filed May 6, 2008, issued as U.S. Pat. No. 9,622,694 on Apr. 18, 2017, which is a continuation-in-part of U.S. patent application Ser. No. 29/281,301, filed Jun. 20, 2007, issued as U.S. Pat. No. D568,479 on May 6, 2008, and Ser. No. 29/305,102, filed Mar. 13, 2008, issued as U.S. Pat. No. D587,375 on Feb. 24, 2009. These applications are incorporated by reference along with all other references cited in this application.

BACKGROUND OF THE INVENTION

The present invention relates to medical devices and their manufacture. More particularly, the present invention relates to patient monitoring devices and methods.

Patient monitoring systems measure, display, and sometimes store physiological data. Patient monitoring systems are now used in a wide variety of applications. This includes, for example, hospital, ambulatory, and home health care. Hospitals routinely measure and analyze the vital signs of surgical, trauma, and other patients from admission through discharge. There are many different types of monitoring devices. For example, there are monitoring devices for blood pressure, body temperature, heart activity, blood gases, cholesterol, glucose, pulse rate, respiration rate, tissue oxygen saturation, and many other parameters.

Noninvasive monitoring devices fulfill an important role in assessing, tracking, diagnosing, and treating patients. These devices enable early diagnosis, treatment of acute conditions, and reduce the need for invasive interventions. Some types of monitoring devices gather patient data via sensors attached to the patient.

Near-infrared spectroscopy has been used for noninvasive measurement of various physiological properties in animal and human subjects. The basic principle underlying the near-infrared spectroscopy is that physiological tissues include various highly-scattering chromophores to the near-infrared waves with relatively low absorption. Many substances in a medium may interact or interfere with the near-infrared light waves propagating therethrough. Human tissues, for example, include numerous chromophores such as oxygenated hemoglobin, deoxygenated hemoglobin, water, lipid, and cytochrome, where the hemoglobins are the dominant chromophores in the spectrum range of approximately 700 nanometers to approximately 900 nanometers. Accordingly, the near-infrared spectroscope has been applied to measure oxygen levels in the physiological medium such as tissue hemoglobin oxygen saturation and total hemoglobin concentrations.

There is, then, a continuing demand for medical devices that are more sensitive, easier to use, safer to use, provide more features, and generally address the needs of patients, doctors, and others in the medical community. For example, current near-infrared devices have difficulty detecting various properties of deep layer tissue, such as the brain.

Therefore, there is a need to provide improved systems and techniques for monitoring patients.

BRIEF SUMMARY OF THE INVENTION

The present invention relates to patient monitoring devices. In an embodiment, the invention uses cerebral tissue oxygen saturation measurements to assess oxygen supply and blood circulation in the brain for the purpose of guiding cardiac surgeries or other types of surgeries that may affect oxygen supply and blood circulation in the brain. Cerebral tissue oxygen saturation measurement may be determined by combining a two-layer model and an automatic error cancellation scheme. The invention may obtain a tissue oxygen saturation measurement of a tissue layer that is covered by another layer of tissue.

In an embodiment, the invention is a device including a first source structure, a first near detector structure, a first far detector structure, and a light diffusing layer, where the first near detector structure receives a beam of light after the beam of light has been transmitted through a tissue and the light diffusing layer. The first source structure, first near detector structure, and first far detector structure may be arranged in a line.

A first distance between the first source structure and the first near detector structure may be different from a second distance between the first source structure and first far detector structure. The first distance may be less than the second distance. The first distance may be approximately 30 millimeters. The second distance may be approximately 40 millimeters.

The device may further include a second source structure, a second near detector structure, and a second far detector structure, where the second near detector structure receives the beam of light after the beam of light has been transmitted through the tissue and the light diffusing layer. The second source structure, second near detector structure, and second far detector structure may be arranged in a line.

A third distance between the second source structure and the second near detector structure may be different from a fourth distance between the second source structure and second far detector structure. The third distance may be less than the fourth distance. The third distance may be approximately 30 millimeters. The fourth distance may be approximately 40 millimeters.

In an embodiment, the light diffusing layer may be a semitranslucent film. In an embodiment, the first near detector structure, the second near detector structure, the first far detector structure, and the second far detector structure may comprise photodiodes. The first source structure and second source structure may comprise optical fiber.

In an embodiment, the invention is a method including positioning a sensor head to face toward a tissue, where the sensor head comprises a first source structure, a second source structure, a far detector arrangement, a near detector arrangement, and a semitranslucent film covering the near detector arrangement. Transmitting light through the first source structure and the second source structure into a tissue. Receiving light transmitted through the tissue and the detector arrangement, the received light including attenuation characteristics, and processing the received light using a system unit.

The light may be transmitted from the system unit. Receiving the light transmitted through the tissue may be through photodetectors at the sensor head. The attenuation characteristics may be at least partially caused by the semitranslucent film.

In an embodiment, the invention is a probe, the probe being adapted for use as a part of a medical device system for measuring oxygen levels in a tissue. The probe includes a sensor pad having a first cavity, a second cavity, and a third cavity, where a semitranslucent film is coupled to a bottom surface of the sensor pad and partially overlaps the first cavity. The probe further includes a sensor arrangement which includes a plurality photodetectors coupled to the first cavity, a first source structure coupled to the second cavity, and a second source structure coupled to the third cavity.

In an embodiment, the invention is a method including placing a sensor head on a surface of a tissue to be measured and transmitting light through a plurality of sources of the sensor head into the tissue. The method further includes receiving light transmitted through the tissue at a first set of detectors and at a second set of detectors, where the received light has a first attenuated amount at the first set of detectors and a second attenuated amount at the second set of detectors. The method further includes using the first attenuated amount, to calculate a first attenuation coefficient for a shallow tissue region having a depth of at most about X below the surface of the tissue and using the second attenuated amount and the first attenuation coefficient calculate a second attenuation coefficient for a deep tissue region having a depth of at least about Y below the surface of the tissue.

In the method above, in a specific embodiment, X is the same as Y, or X is less than Y. In various different embodiments, however, X is the same as Y, X is different from Y, X is less than Y, or X is greater than Y, and any combination of these.

In a specific embodiment, X and Y are about 12 millimeters. Depending on the person (e.g., adult, child, male, female, human, or animal), X and Y may range from about 6 millimeters to 20 millimeters, from about 6 millimeters to 40 millimeters, and any number in these ranges (e.g., 8, 10, 11, 13, 14, 15, 16, 17, 18, 19, 20, 25, 35, 36, or 38) between. The tissue may include a human scalp, skull, and brain. The second attenuated amount may be omitted when calculating the first attenuation coefficient. Calculating the second attenuation coefficient may be performed after calculating the first attenuation coefficient. The second attenuated amount may be greater than the first attenuated amount.

A near distance from the set of sources to the first set of detectors may be less than a far distance from the set of sources to the second set of detectors.

In an embodiment the plurality of sources includes a first source structure and a second source structure, and the first plurality of detectors includes a first detector structure and a second detector structure. The first source structure, second source structure, first detector structure, and second detector structure are arranged to define vertices of a quadrilateral. A first side of the quadrilateral between the first source structure and first detector structure is same in length from a second side of the quadrilateral between the second source structure and the second detector structure. In a specific implementation, the quadrilateral is convex.

In an embodiment the plurality of sources includes a first source structure and a second source structure, and the first plurality of detectors includes a first detector structure and a second detector structure. The first source structure, second source structure, first detector structure, and second detector structure are arranged to define vertices of a quadrilateral. A first side of the quadrilateral between the first source structure and first detector structure is different in length from a second side of the quadrilateral between the second source structure and the second detector structure. In a specific implementation, the quadrilateral is convex.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 11a shows the sensor placed on a right side of a patient's forehead.

FIG. 11b shows the sensor placed on a left side of a patient's forehead.

DETAILED DESCRIPTION OF THE INVENTION

Figure 1:
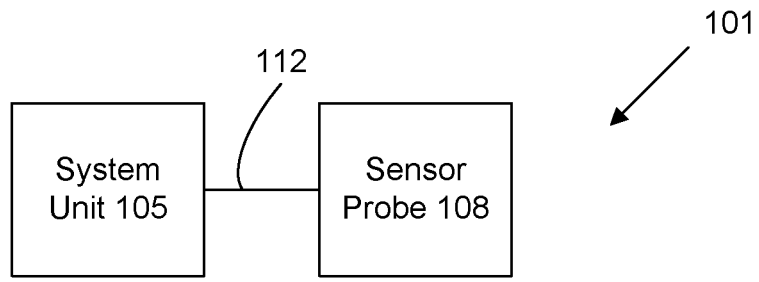
FIG. 1 shows an oximeter system for measuring oxygen saturation of blood in a patient.

FIG. 1 shows an oximeter system 101 for measuring oxygen saturation of blood in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers). In other implementations of the invention, however, connection 112 may be wireless such as via a radio frequency (RF) or infrared communication.

Typically, the system is used by placing the sensor probe in contact or close proximity to tissue (e.g., skin) at a site where an oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery and patient monitoring such as during patient transport. Applications may also include use with intensive care patients, nursing home patients, and patients with acute illnesses. The tissue oximeter can make oxygen saturation measurements of tissue where there is no blood flow or pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbances of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Figure 2:
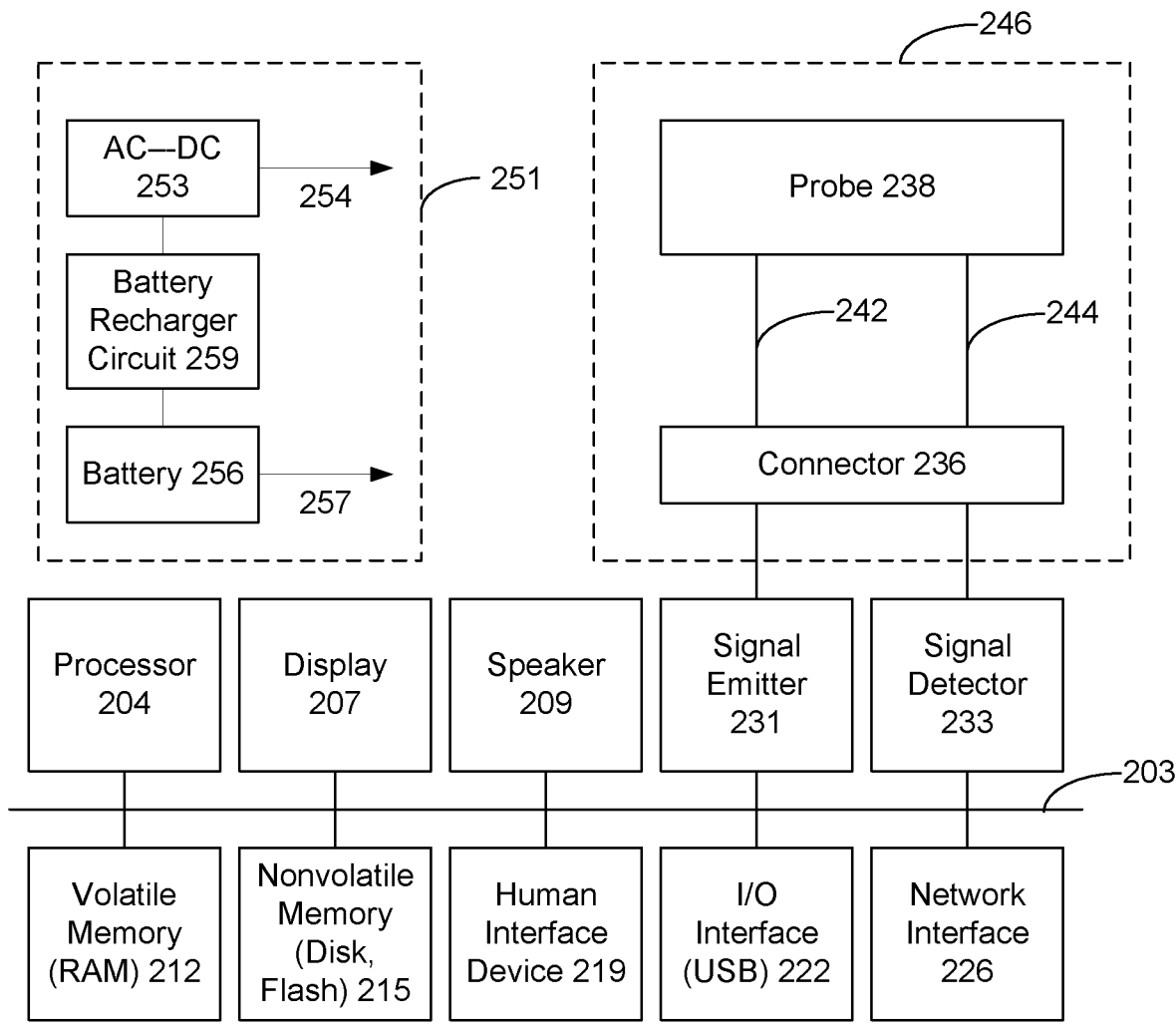
FIG. 2 shows in greater detail, a block diagram of a specific implementation of the system in FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

The connector may have a locking feature; e.g., insert connecter, and then twist or screw to lock. If so, the connector is more securely held to the system unit and it will need to be unlocked before it can be removed. This will help prevent accidental removal of the probe.

The connector may also have a first keying feature, so that the connector can only been inserted into a connector receptacle of the system unit in one or more specific orientations. This will ensure that proper connections are made.

The connector may also have a second keying feature that provides an indication to the system unit which type probe of probe is attached. The system unit may handle making measurements for a number of different types of probes. The second keying feature will let the system unit know which type of probe is connected, so that it can perform the right functionality, use the proper algorithms, or otherwise make adjustments its the operation for a specific probe type.

In various implementations, the system is powered using a wall outlet or battery powered, or both. Block 256 shows power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
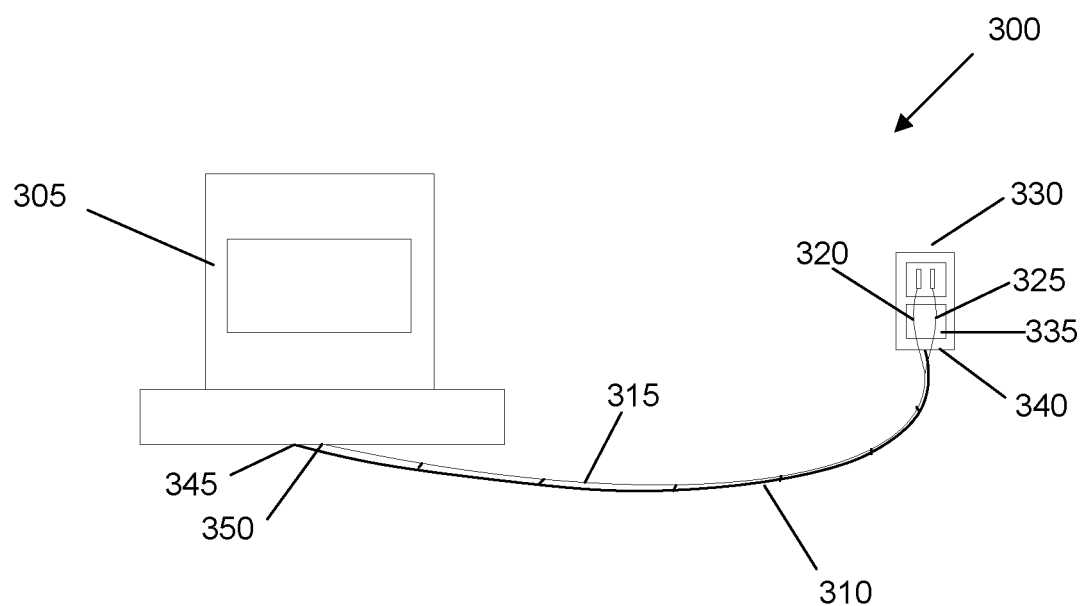
FIG. 3 shows an optical imaging system in accordance with an embodiment of the present invention.

FIG. 3 shows a system 300 of the invention including a monitoring console 305, cables 310, 315, 320, and 325, and a sensor 330. Sensor 330 includes a sensor unit (i.e., sensor head) 335 and a sensor housing 340.

Connectors 345 and 350 at an end of cables 315 and 310, respectively, connect the sensor to the monitoring console.

The length of the cables may vary. In a specific implementation, the length of the cables ranges from about 1.2 meters to about 3 meters. For example, the cables may be about 1.3, 1.4, 1.5, 1.6, 1.7, 1.8, 1.9, 2, 2.1, 2.2, 2.3, 2.4, or 2.5 meters long or greater. Depending on the specific application, the cable lengths may be less than 1.2 meters. In some applications, the cable lengths will be greater than 3 meters.

A specific application of the invention is operating room use or other places where it is desirable to maintain cleanliness and sterile conditions, such as isolation units. Patients in isolation units may have contagious diseases or compromised immune systems. Hospitals need to ensure that patients with a contagious disease do not infect others. Items introduced near the patient must either be disposed after use or properly cleaned. Hospitals also need to protect patients with compromised immune systems from sources of microorganisms. In these cases, a longer cable length, such as greater than 1.2 meters, is advantageous because this helps to separate the patient from sources of contamination, such as the console. Similarly, a longer cable length also minimizes contamination, such as contamination of the console, by the patient.

The sensor including the sensor housing and sensor unit, entire length of cables and the connectors are packaged as a probe unit in a sterile package. The probe unit is detachable from the console after use and may be disposed. A user may then open a new sterile package containing a new probe unit. The package may be opened at the time of actual use or near the time of actual use so as to not contaminate the probe unit. The user can then connect this new and sterile probe unit to the console to begin monitoring. This disposable feature provides an additional level of protection in maintaining a sterile field around the patient.

Short cables pose a problem. Short cables bring whatever element they are connected to within close proximity to the patient. Doctors and nurses must then devote additional care and time to ensure a sterile field around the patient. This may include, for example, additional cleansing of the elements before and after introduction to the sterile field, or sterile drapes on the elements.

In a specific embodiment, there may be other connectors on the cables besides connectors 345 and 350. These other connectors allow the cables to be separated into multiple pieces. The cables attached to the sensor can then be disposed along with the sensor after use. The cables attached to the console can be reused.

In an implementation, cables 320 and 325 include one or more optical wave guides enclosed in a flexible cable jacket. The optical wave guides may be used to transmit light from the console and into the tissue. The optical wave guides may have the shape of a polygon, such as a square, rectangle, triangle, or other shape. In other cases, the optical wave guides may have circular or oval shapes. In a specific implementation, the optical wave guides are multiple strands of fiber optic cable. The flexible cable jacket may be thin-walled PVC with or without an aluminum helical monocoil, shrink wrap tubing, plastic, rubber, or vinyl.

In a specific embodiment, all of the fiber optic cables are enclosed within one end, or both ends of the flexible cable jacket. Minimizing the number of exposed cables lowers the likelihood that the cables will get entangled. In another embodiment, the fiber optic cables are not enclosed together and instead each fiber optic cable is enclosed in its own flexible cable jacket.

In a specific implementation, cables 320 and 325 are passive. For example, they will not contain any active, generative properties to maintain signal integrity. However, in other implementations, the cables may include active components. The cable may include active components to amplify the signal at the sensor unit. For example, long lengths of cable subject to significant attenuation may require amplification. Amplification may also be required if the monitored site contains a particularly dense structure such as bone. In a specific implementation, radiation sources such as light emitting diodes (LEDs) may be placed in the sensor. Thus, the cables may contain electrical wiring to transmit power to the radiation sources.

In an implementation, cable 310 is standard electrical wiring (e.g., copper or aluminum wire), which is stranded or solid core, or coaxial cable, or any combination of these. Cable 310 itself may contain multiple electrical wires. Further, the cable may also include a combination of one or more optical wave guides and electrical wiring. In a specific embodiment, the electrical wiring and each optical wave guide may be enclosed in their own separate flexible cable jacket. In another embodiment, multiple optical wave guides may be enclosed in a flexible cable jacket, separate from the cable jacket enclosing the electrical wiring. For example, cables 325 and 320 may be enclosed in a cable jacket to form cable 315, while cable 310 is enclosed in a separate cable jacket. In yet another embodiment, both the optical wave guides and electrical wiring will be enclosed in the same flexible cable jacket. For example, cables 325, 320, and 310 may be enclosed in the same cable jacket.

In an embodiment of the invention, each opening on the sensor unit and corresponding cable is dedicated to a particular purpose. For example, a first opening on the sensor unit (and corresponding fiber optic cable) is dedicated to transmitting light from the monitoring console. A second opening on the sensor unit is dedicated to transmitting a signal received at the second opening to the monitoring console.

Some embodiments use a particular opening and cable for multiple purposes (e.g., both input and output) using a scheme such as multiplexing.

In a specific embodiment, a particular opening and cable transmits an output to affect a reaction (e.g., sending electrical signals to stimulate muscle or other tissue). Another opening and cable transmits the resultant signal back to the monitoring device. In yet another embodiment, the openings and cables may simply detect changes and transmit these changes back to the monitoring device. For example, the openings and cables may carry voltage changes in the patient's skin back to the monitoring device.

In an implementation, the connectors on the cables and monitoring console have indicators. The indicators may be color indicators that are painted on, or raised indicators, or both. These indicators help the user to properly attach the cables to the monitoring console. For example, the indicators may include green arrows placed on the cable connectors and monitoring console. Alignment of the arrows indicates proper attachment of the cables. Further, there may be instructions printed on the console, cables, or both that instruct the user on the proper attachment of the cable.

The connectors at the end of the cables attach to the monitoring console and protect the cables from accidental disconnection. The connector may be a threaded collar on a cable end that threads onto the monitoring console. Alternatively, the connector may be a lug closure, press-fit, or snap-fit.

In an implementation, the console is portable. Thus, the console can be hand-carried or mounted to an intravenous (IV) pole. A portable console can follow a patient anywhere in the hospital, eliminating the need to change connections whenever a patient is moved. Moreover, a portable design facilitates use and assessments in numerous other locations besides a hospital.

A portable console is typically battery-operated. The battery is typically a rechargeable type, such as having nickel cadmium (NiCd), nickel metal hydride (NiMH), lithium ion (Li-Ion), lithium polymer, lead acid, or another rechargeable battery chemistry. The system can operate for a certain amount of time on a single battery charge. After the battery is drained, it may be recharged and then used again.

The portable console may also have a power-saving feature. This reduces battery consumption during continuous measurements. The power-saving feature may, for example, darken the console's display screen after a certain time of inactivity. The time may be approximately five, ten, fifteen, or twenty minutes. Alternatively, the user may program the time.

In a specific implementation, the portable console weighs approximately 4.3 kilograms. However, the weight may vary from about 3 kilograms to about 7 kilograms including, for example, 3.5, 4, 4.5, 5, 5.5, 6, 6.5, or more than 7 kilograms.

In another implementation, the console is not hand-held or portable. The console may be a large, nonportable device that is attached to a wall or secured to a stand or surface. In this implementation, the system is typically connected to AC power. A battery may be used as a back-up to the AC power.

In a specific implementation, the console provides alerts. The alerts may be visual (e.g., a flashing light on a display of the console), audible, or both. Visual alerts may be designed so that they are viewable from any location (e.g., a flashing light on the top of the console). In a chaotic and noisy situation, this allows users to quickly respond to a patient. These alerts may signal a problem with the system. This includes, for example, insufficient signal strength, kinks or sharp bends in the cable, debris on the sensor unit, debris on a coupling surface between the cable and the console, insufficient electrical power, a low battery, an improperly attached cable, or other problem.

An alert may also signal when the system is ready for patient monitoring. The alerts may also provide warnings at certain oxygen saturation levels. Different alerts may be used depending on the type of problem detected by the system. Different alerts include different colors, sounds, and intensities of colors and sounds.

The console may provide an alert when the sensor unit is placed in a suitable location for a measurement. The alert may vary in intensity depending on the suitability of the location. The alert may be audible, or visual, or both. An audible alert allows the user to determine the suitability of a location without having to look away from the patient.

The alerts may be user-programmable. That is, users may set which alerts are enabled, the threshold at which they are activated, and the intensities of the alerts. For example, a user may decide to enable the oxygen saturation alert, set the alert to occur if and when the oxygen saturation level falls below a certain value, and set the volume level of the alert.

The console may also include a mass storage device to store data. Mass storage devices may include mass disk drives, floppy disks, magnetic disks, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, oxygen saturation measurements and the time and date measured. The oxygen saturation measurements may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

A screen on the console displays the patient's data. The screen may be a flat panel display such as a liquid crystal display (LCD), plasma display, thin film transistor liquid crystal display (TFT LCD), electro-luminescent (EL), or organic light emitting diode (OLED) display. The screen may include a touch screen interface. Such touch screen interfaces are easier to clean compared to keypads if they become contaminated because they do not contain mechanical parts.

The screen may display numbers, text, graphics, and graphical trends in color. Different colors may correspond to different measurements or threshold levels. The text and numbers may be displayed in specific languages such as English, Spanish, French, Japanese, or Tagalog. The displayed language is user-programmable.

In a specific implementation, the screen displays data related to a single regional oxygen saturation reading. For example, this may include a single plot or graph.

Users can also vary the size of the displayed information on the console's screen. This allows the display to be viewed at a distance, increases the viewing angle, and allows users with vision limitations to see the information.

In a specific implementation, the console includes one or more near-infrared radiation sources. In other implementations, the radiation sources may be external to the console. For example, the radiation sources may be contained within a separate unit between the console and sensor. In yet another implementation, some radiation sources may be within the console while other radiation sources are external to the console.

These radiation sources may be near-infrared lasers. In a specific implementation, there are four near-infrared lasers located within the console. In other implementations, there may be less than four radiation sources or more than four radiation sources. For example, there may be 2, 3, 5, 6, 7, 8, 9, 10 or more than 10 radiation sources. These radiation sources may generate approximately 100 milliwatts of power. This allows photodiodes, which in an implementation are located at the sensor, to receive light where the signal-to-noise ratio is greater than 10. However, the power can range from about 70 milliwatts to about 130 milliwatts. For example, the power may be 75, 80, 85, 90, 95, 100, 105, 110, 115, 120, 125, or more than 130 milliwatts. Depending on the application, the power may be less than 75 milliwatts such as 30 milliwatts.

Figure 4:
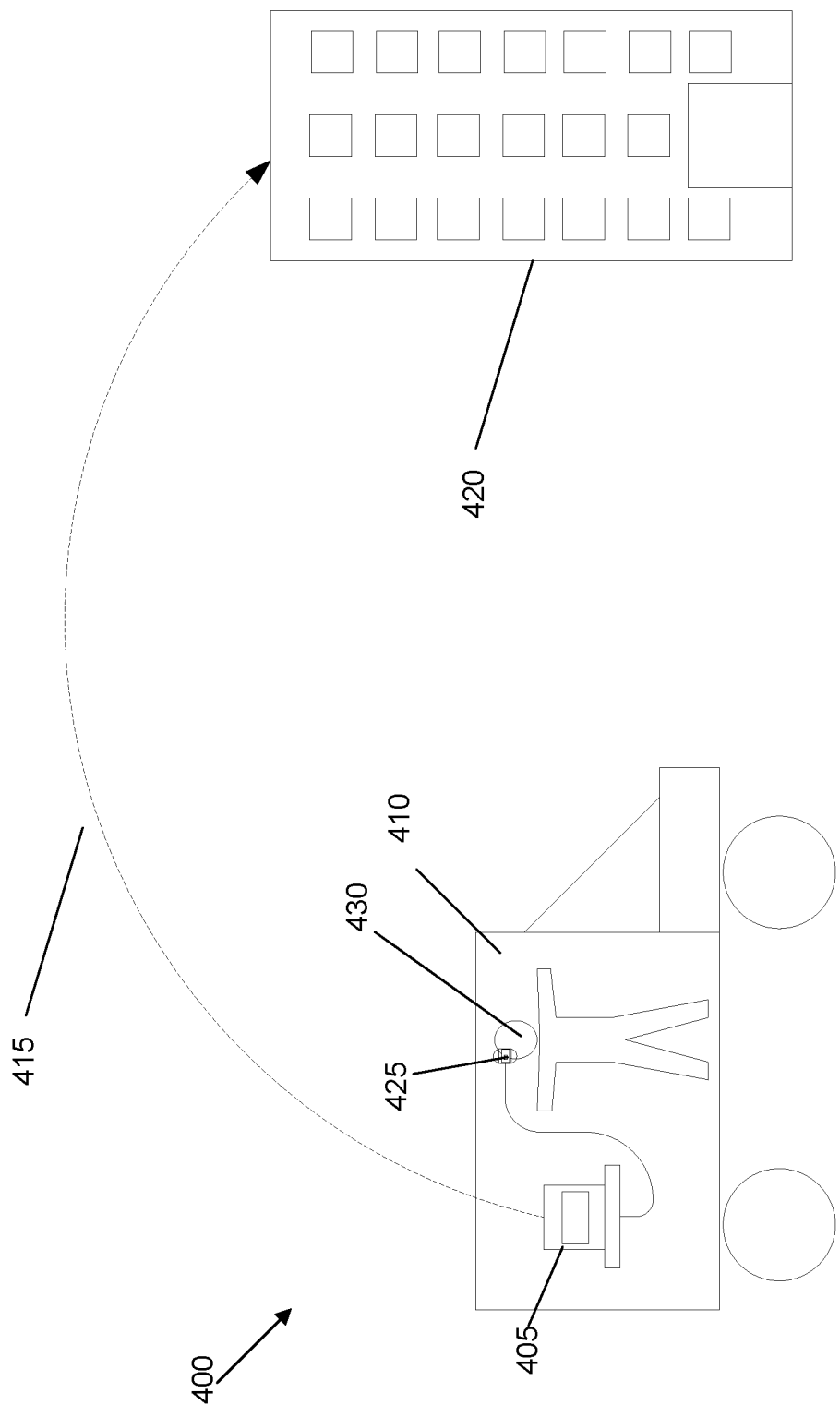
FIG. 4 shows the wireless transfer of patient data from a field location to a receiving location.

FIG. 4 shows an example of a wireless implementation of the invention. A system 400 includes a monitoring console 405 at a field location 410 which transmits 415 the patient's data to a receiving location 420. The figure shows the monitoring console transmitting the data, using for example, a modem in the monitoring console. However, in another implementation, a sensor unit 425 may wirelessly transmit the data the receiving location.

In the figure, the field location is in an ambulance. The ambulance is transporting a patient 430 to a hospital. In other implementations, the field location may be in another type of vehicle such as a car, automobile, truck, bus, train, plane, boat, ship, submarine, or helicopter. The field location may also be on a battlefield, at an accident scene such as a car accident, at a natural disaster scene such as an earthquake, hurricane, fire, or flood, in a patient's home, at a patient's place of work, or in a nursing home.

The receiving location also varies. The receiving location may be a hospital, clinic, trauma center, physician's home or office, or a nurse's home or office. The monitoring console or sensor unit may also transmit to multiple receiving locations. For example, data may be transmitted to both the hospital and the physician's home.

A variety of devices may receive the data. This includes, for example, a monitoring console, other monitoring stations, mobile devices (e.g., phones, pagers, personal digital assistants (PDAs), laptops), or computers, or combinations of these.

The distance between the field and receiving location may vary. The field and receiving location could be in different countries, states, cities, area codes, counties, or zip codes. In other cases, the field location and receiving location may be in different parts of the same room or in different rooms in the same building.

The wireless transmission may be analog or digital. Although FIG. 4 shows the system transmitting data directly to the receiving location, this is not always the case. The system may relay data to the receiving location using intermediaries. For example, satellites may rebroadcast a transmission. While in one embodiment, a communication network is the Internet, in other embodiments, the communication network may be any suitable communication network including a local area network (LAN), a wide area network (WAN), a wireless network, an intranet, a private network, a dedicated network, phone lines, cellular networks, a public network, a switched network, and combinations of these and the like. Wireless technologies that the system may employ include: Wi-Fi, 802.11a, 802.11b, 802.11g, 802.11n, or Bluetooth, or combinations of these and the like. The system also has the ability to switch from one communication technique to another if, for example, the current network is unreliable or there is interference. The switch may either be automatic or manual.

The system's ability to wirelessly transmit data offers several advantages. It reduces the time to treatment for a patient. For example, data sent from an ambulance en route to a hospital allows a physician at the hospital to mobilize personnel and equipment before the patient even arrives. Another advantage is long-distance monitoring. For example, patients may use the system in their own homes. The system will then, on a continuous basis if desired, transmit data to a receiving location, such as a hospital. A nurse or physician at the hospital can then review the data. If the data indicates a problem with the patient, then the hospital can dispatch an ambulance to the patient's home.

Figure 5:
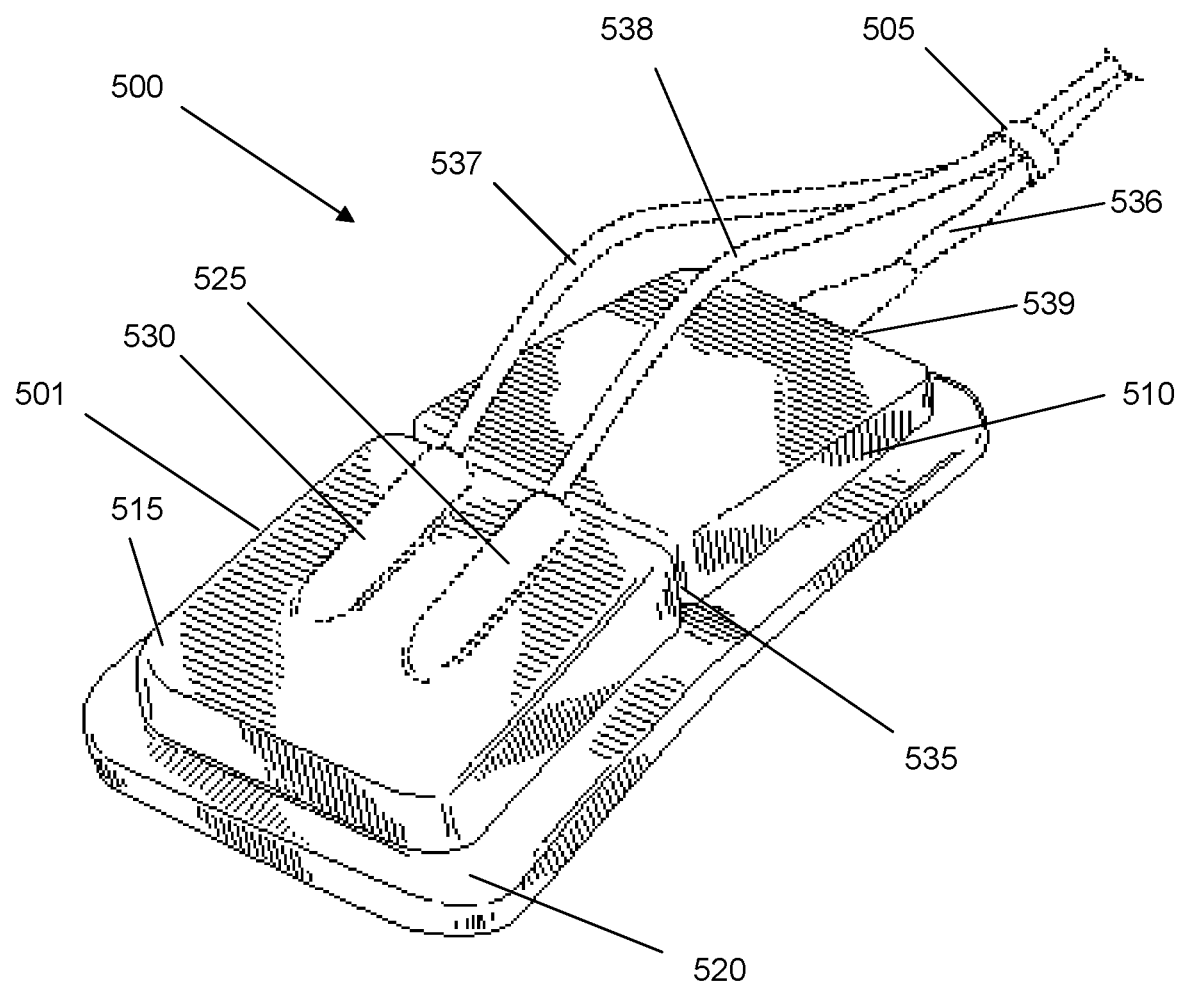
FIG. 5 shows a perspective view of a sensor.

FIG. 5 shows a perspective view of a sensor 500 in accordance with an embodiment of the present invention. Sensor 500 includes a sensor housing 501. The sensor housing includes a detector housing 510, a source housing 515, and a base 520. The detector and source housings are coupled to the base. A small separation 535 exists between the detector and source housings. In a specific implementation, a cable 536 enters an edge 539 of the detector housing. Cables 537 and 538 enter the top surface of the source housing. Cable fastener 505 fastens the cables together.

Cables 537 and 538 each enter the top surface of the source housing and through cavities in the source housing. In other implementations, one or both cables may enter at an edge of the source housing. Within each cavity is a source structure that the cables enter. The cavities are exposed through an opening on the bottom surface of the base. The cables are secured to the top surface of the source housing with, for example, an adhesive. The adhesive may be a tape, a glue such as epoxy, or a sealant such as a silicon sealant. Stitches may also be used to secure the cables.

In the implementation shown, cable 536 enters through edge 539 of the detector housing. In other implementations, cable 536 may enter through the top of the detector housing. Cable 536 enters through a cavity in the detector housing and connects to detector structures (not shown) which are embedded the detector housing. Cable 536 is secured to the sensor housing with, for example, an adhesive. The adhesive may be a tape, a glue such as epoxy, or a sealant such as a silicon sealant. Stitches may also be used to secure the cable.

In a specific embodiment, the sensor housing is made of foam, specifically, one or more pieces of ⅛-inch (3.18 millimeters) thick cross-linked polyethylene foam coated on one side with a medical-grade adhesive (e.g. pressure sensitive medical-grade acrylic adhesive) with a white release liner (e.g., 92 pound, bleached kraft paper, polycoated, silicone treated on one side), such as that made by Scapa North America of Windsor, Connecticut and available as part number 0399003. In this specific embodiment, thickness of the foam is determined under American Society for Testing Materials (ASTM) D1005-95.

In this specific embodiment, the adhesive properties may further include a thickness of 1.5 mils as determined under ASTM D1000-93, a value of tearing bond for adhesion to steel, and a value of tearing bond for adhesion to backing as determined under the Pressure Sensitive Tape Council (PSTC) test method number 1 with a 30 minute dwell time.

In other embodiments, the sensor housing is made of polystyrene, paper, corrugated fiberboard, polypropylene, polyurethane, an inflated air pillow, silicon, latex, rubber, or molded pulp. The sensor housing may have a 20 to 60 type A durometer.

Furthermore, the individual parts of the sensor housing may be made of different materials. For example, the base may be made of polyethylene foam while the source and detector housing is made of rubber.

In an implementation, the detector housing, source housing, and base all have the shape of a polygon. For example, the base may have the shape of a rectangle with rounded corners. The detector housing and source housing may have the shape of a square with rounded corners. However, in other implementations, the shapes may not all be composed of generally straight line segments. For example, the shapes may include convex edges and thus resemble circles, ovals, or ellipses. The shapes may also include concave edges and combinations of concave edges, convex edges, and straight edges.

In an implementation, the sensor housing is flexible. The flexibility allows the sensor housing to conform to the shape of the sensor unit (i.e., detector and source structures) and the patient's skin. This allows the sensor unit to be shielded from ambient light. Source light is also prevented from escaping. The sensor unit uses light transmitted by an optical wave guide, such as a fiber optic cable, to obtain sensitive measurements. If light from the sensor unit escapes through the sensor housing, the sensor unit may not detect this light. Likewise, ambient light entering the sensor housing will also result in inaccurate readings. When the sensor housing conforms it creates a dark environment within the sensor housing that enables accurate readings. The sensor housing's flexibility is a function of its size and material type.

In an implementation, one or more light-shielding layers may be included with the sensor housing to shield ambient light and to protect source light from escaping. These light-shielding layers may be constructed of polypropylene film metalized with aluminum and coated with a pressure sensitive adhesive. In other implementations, the layers are made of a foil, a mirror, or made of other materials such as gold, titanium dioxide, or a composite of materials to block or reflect light. Other examples include a light-reflective tape, a material coated with light-shielding paint, a material impregnated with light-reflective material, or a light-reflective fabric. The sensor unit itself may be covered or made with a light-reflective material.

Small separation 535 may be located at approximately a midpoint of the sensor housing. The separation may be about 0.5 millimeters to about 5 millimeters. For example, the separation may be 0.6, 0.7, 0.8, 0.9, 1, 2, 3, 4, or 6, or more than 6 millimeters. In other applications, the separation will be less than 0.5 millimeters. The separation is located between the detector and source housings. The sources are on one side of the separation while the detectors are on the other side of the separation. The separation allows the base to easily fold inward such that the source and detector structures are angled in towards each other. This allows the detectors to better receive the light after it has been transmitted through the tissue.

The separation also allows the base to more easily conform to curved surfaces, such as the curved surface of a patient's forehead. Moreover, the increased flexibility allows the sensor to be used on a variety of surfaces which have varying degrees of curvature. In an implementation, the sensor is placed on a patient's forehead to measure cerebral tissue oxygen saturation. Some foreheads are flat and other foreheads are more rounded. The sensor, because of its flexibility, may be equally effective on either forehead.

In other implementations, a cut, score, or perforations in the sensor housing may be used to impart an additional degree of flexibility. The cut, score, or perforation may be made at a midpoint on the top surface of the sensor, between the source and detector structures, or at some other location. For example, the source and detector housings may be a single unit. That is, the source and detector structures may be embedded in a single piece of foam. A score on the top surface of the foam, between the source and detector structures will allow the sensor to conform to a curved surface as the source and detector will bend around this score.

The figure shows the sensor as a single integrated unit. An advantage of using a single sensor probe pad is to lower the cost (i.e., half the cost of using two such pads) and also to make it easier to use. A user does not have to position or otherwise manipulate or align multiple sensors to attach to a patient. However, depending on the situation and patient (e.g., patient that has slight thicker skull), then a multiple sensor pad arrangement discussed below could be used.

Also, the arrangement of the sources and detectors are such that the pad has a compact structure and will not run across a person's forehead.

Figure 6:
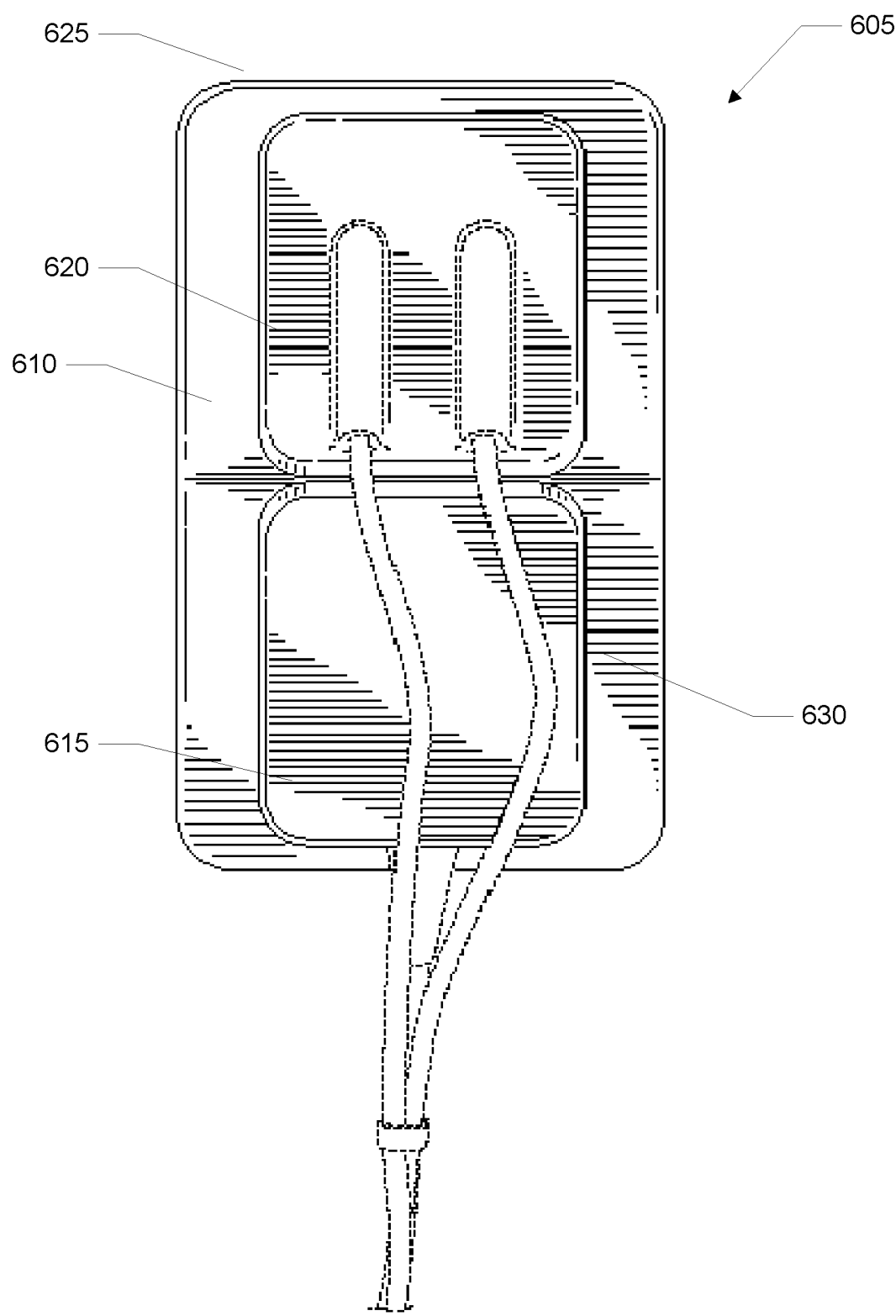
FIG. 6 shows a top view of the sensor.

FIG. 6 shows a top view of a sensor 605. A base 610 extends past edges of a detector housing 615 and a source housing 620.

The base may extend past the edges from about 1 millimeter to about 10 millimeters. For example, the extension may be about 2, 3, 4, 5, 6, 7, 8, or 9 millimeters, or more, or less than 1 millimeter. In a specific implementation, the base may not extend past the edges of the detector and source housing. Instead, the edge of the base may overlap with edges of the detector and source housing. In other implementations, the base only extends past one, two, or three edges of the detector and source housing.

In a specific implementation, the base extends past the left and right edges of the detector and source housings for a distance that is greater than the extension past the top edge of the source housing and the bottom edge of the detector housing as shown in FIG. 6. However, this is not always the case. For example, the base may extend past the edges of the source and detector housings by the same amount. In other implementations, the base may extend past the top edge of the source housing and the bottom edge of the detector housing for a distance that is greater than the extension past the left and right edges of the detector and source housings.

The edges of sensor may serve as locator guides. In an implementation, the user places the sensor on the patient's forehead such that an edge 625 is approximately 1 centimeter away from the midline of the patient's forehead. An edge 630 may also used as locator guide. For example, edge 630 may be placed on the patient's forehead such that edge 630 is approximately 1 centimeter above the patient's eyebrow. When the device is properly attached, the patient should not feel strong light which is a sign of being away from the patient's frontal sinus.

In a specific implementation, there may be instructions including text, diagrams, or both printed on the sensor housing that instruct the user on the proper placement of the sensor. The text, diagrams, or both may include a ruler in English units, metric units, or both to help the user properly position the sensor.

Figure 7A:
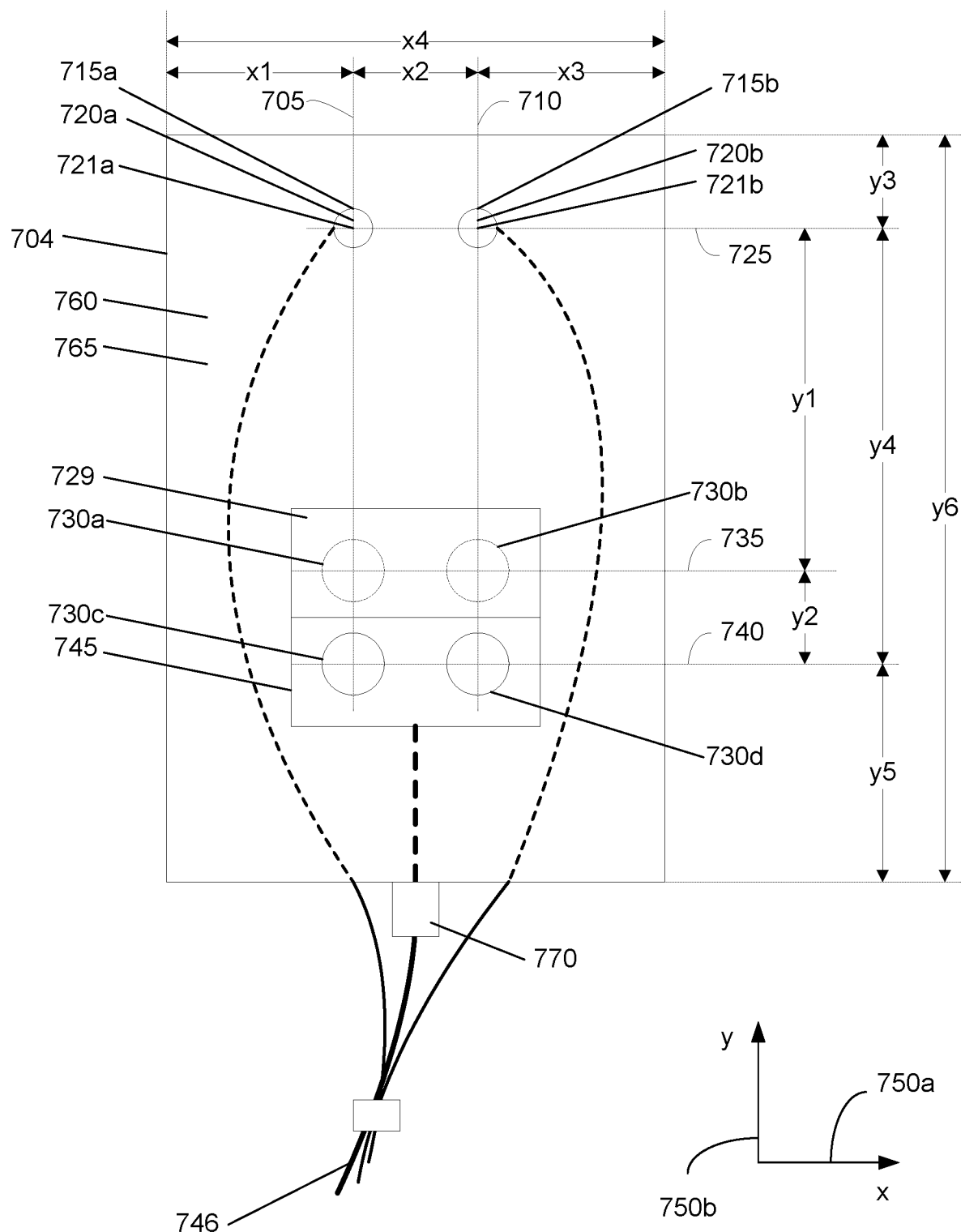
FIG. 7a shows a bottom view of an implementation of a symmetrical sensor.

FIG. 7*a* shows a bottom view of the sensor. In a specific implementation, a sensor housing base 704 has openings 720*a*, 720*b*, and 745. Openings 720*a* and 720*b* are coupled to cavities 721*a* and 721*b*. Source structures 715*a* and 715*b* may be located in cavities 721*a* and 721*b*, respectively, and are exposed through the openings.

Detector structures 730*a*, 730*b*, 730*c*, and 730*d* occupy cavity 745 and are exposed through opening 745. A light diffusing layer 729 covers detector structures 730*a* and 730*b*. An adhesive film 760 covers the bottom surface of the sensor housing base. A release liner 765 with a pull-tab 770 covers the adhesive film.

In a specific implementation, the sensor unit includes source structures 715*a* and 715*b* and detector structures 730*a*, 730*b*, 730*c*, and 730*d*. In one embodiment, the source structures, detector structures, or both may be packaged into a single reusable physical unit while the sensor housing is separately packaged as disposable physical unit. Separating the source and detector structures from the sensor housing offers several benefits. For example, the source structures may include laser diodes and the detector structures may include photodiodes. These elements may be more expensive than the sensor housing which is typically made of foam. Reusing the more expensive elements may allow for significant cost savings. Disposing the less costly sensor housing after use and replacing with a new sensor housing from a sterile package protects the patient from contamination.

In another embodiment, they may not be packaged into a single physical unit. For example, the source structures may be packaged in a physical unit that is separate from the detector structures. In yet another embodiment, there is no physical packaging of source structures and detector structures. Instead, each source structure may be individually placed in the sensor and likewise, each detector structure may be individually placed in the sensor.

The implementation shown has a total of three openings (720*a*, 720*b*, and 745) on the sensor housing base. In other implementations, there may be more or less openings. For example, there may be one or two openings or three, four, five, six, seven, eight, or more than eight openings.

In the implementation shown, the two source structures each have their own opening. The four detector structures are grouped together in a single opening. However, this is not always the case. The sources may be grouped together in a single opening while the detectors may each have their own separate opening. In another embodiment, all the sources and detectors may be grouped together into a single opening. In yet another embodiment, each source and each detector may have their own opening.

In a specific embodiment including fiber optic cables, one fiber optic cable connects to each source opening on a bottom surface of the sensor unit. The bottom surface faces and contacts the area of the person, animal, or other living thing that is being monitored. There is any number of source openings. This includes, for example, one, two, three, four, five, six, seven, eight, or more than eight source openings. For example, if the bottom surface has two source openings there will be two fiber optic cables for transmitting radiation from the monitoring console. Similarly, if the bottom surface has six source openings, there will be six fiber optic cables.

In a specific implementation, each source structure includes a strand of fiber optic cable to transmit light into the tissue while each detector structure includes a photodiode to receive the transmitted light. For example, opening 715*a* holds one end of a first fiber optic cable while opening 715*b* hold one end of a second fiber optic cable. Each dectector structure 730*a*, 730*b*, 730*c*, and 730*d* has a photodiode.

By having the photodiode (or photodetector) embedded in the sensor probe housing, instead of using just an end of a fiber optic cable connected to a photodiode in the system unit, this places each photodiode much closer to the site that is being measured. This allows much more accurate readings and allows detection of signals have a much lower signal strength, such as those transmitted and reflected off of tissue beneath the skull.

Running source signals from one or more signal emitters in the system unit through fiber optic cables provides signals with sufficient strength to penetrate the skull. By having the signal emitters in the system unit, this reduces the cost of the sensor probe. The probe is typically thrown away after one use. Thus, reducing the number of emitters and photodiodes (but having sufficient numbers to allow for accurate measurements) will reduce the cost of a probe.

Electrical wires enclosed in a cable 746 are coupled to each of the embedded photodiodes. Thus, if there are four photodiodes, there will be four electrical signal wires and one ground wire. These electrical wires can then carry the signal generated by the photodiodes back to the console. The signals carried by the electrical wires may include electrical signals converted from the lights received by the detectors. Typically, the power of these electrical signals will be less than 10 milliwatts. Typically, voltage in the wires will be less than 10 volts, and current less than 1 milliamp. However, in other implementations, the power may be greater than or equal to 10 milliwatts. Similarly, the voltage may be greater than or equal to 10 volts and the current may be greater than or equal to 1 milliamp.

In another embodiment, the photodiodes may be external to the sensor. For example, the photodiodes may be located in the console, in a separate unit between the sensor and the console, or there may be a combination of photodiodes that are internal and external to the sensor.

The example in FIG. 7*a* shows all the detector structures (730*a*, 730*b*, 730*c*, and 730*d*) having the same cross-sectional area. In a specific implementation, the cross-sectional area of each detector structure is about 50 square millimeters. However, the cross-sectional area may range from about 45 square millimeters to 55 square millimeters. For example, the cross-sectional area may be 46, 47, 48, 49, 51, 52, 53, or 54 square millimeters. In some implementations, the cross-sectional area will be less than 45 square millimeters. In other implementations, the cross-sectional area will be greater than 55 square millimeters.

Furthermore, in other implementations, the detector structures may not all have the same cross-sectional areas. For example, the detector structures nearest the sources may have a smaller cross-sectional area than the detectors farthest from the sources. In another embodiment, it may be the opposite. That is the detector structures nearest the sources may have a larger cross-sectional area than the detectors farthest from the sources The source and detector structures are typically embedded in the sensor housing such that they do not touch an edge of the sensor housing base. This helps to ensure that light does not escape from the source structures. It also helps to ensure that ambient light is not transmitted to the detector structures. However, in other embodiments, the source and detector structures may touch an edge of the sensor housing base.

In a specific implementation, cable 746 enters at an edge of the sensor at a midpoint between the detector structures and source structures and at an edge nearest the detectors. Thus, cable 746 divides the sensor into a left-hand side and a right-hand side. The left-hand side and right-hand side are mirror images, i.e., they are symmetrical. Each side includes a source structure and two detector structures. In other implementations, the cable may not enter at a midpoint of the sensor. For example, the cable may enter at a different edge near the detectors. In yet another implementation, the cable may enter at an edge that is farthest from the detectors.

In an implementation, light diffusing layer 729 is attached to the bottom of the sensor housing base. It may be attached using an adhesive or it may be embedded within the sensor housing base. The light diffusing layer is typically about 0.1 millimeter thick, but can range from about 0.05 to about 0.2 millimeters. The light diffusing layer typically absorbs about nine-tenths of light at the wavelengths used in a typical implementation of the invention.

In an implementation, the light diffusing layer is permanently attached to the sensor. In other implementations, a user may detach the light diffusing layer and attach a different light diffusing layer having a different size, different optical properties, different thickness, or combinations of these. This allows, for example, the user to customize the sensor according to a particular patient's anatomy.

The example in the figure shows two out of the four detector structures covered by the light diffusing layer. Thus, one-half or 50 percent of the detector structures are covered in this implementation. In other implementations, the percentage may be different. For example, the percentage of detectors covered may be about 5, 10, 20, 30, 40, 50, 60, 70, 80, or 90 percent, or greater.

In the implementation shown, the two detectors covered by the light diffusing layer are the two detectors that are closest to the source structures. In another implementation, the detectors covered by the light diffusing layer may be the detectors farthest from the source structures. In yet another implementation, there may be a different number of detector structures covered by the light diffusing layer including, for example, one, two, three, four, five, six, or more than six detector structures.

The light diffusing layer may be a semitranslucent film having the shape of a polygon, such as a rectangle or square. In another implementation, the shape may include curved edges such as a concave or convex edges. The shape may be an oval, ellipse, or circle. Furthermore, the shape may be a combination of curved and straight edges.

The light diffusing layer may be made of plastic, nylon, crystallized polymers (e.g., polypropylene or polyethylene), polyethylene terephthalate (PET), or glass. In a different implementation, the light diffusing layer may be a film with a pattern of perforations to diffuse the light.

In another implementation, the light diffusing layer may be placed directly on the two detector structures as opposed to being attached to the sensor housing base. The light diffusing layer may be two separate pieces that each has the same shape as the detector structures. Thus, if the detector structures have a circular shape, then the light diffusing layers may be circular as well.

In yet another implementation, the light diffusing layer may be a light-diffusing coating painted onto the detector structures.

The light diffusing layer attenuates the light back-reflected from the shallow layer of the tissue. The shallow layer of the tissue includes the scalp, skull, and cerebrospinal fluid. This helps to make sure that the signal level received by the two near detectors (i.e., detectors 730a and 730b, the detectors nearest the sources) are within the dynamical range of the photodiodes.

In a specific implementation, there may not even be a light diffusing layer. Instead, the back-reflected light may be compensated for through mathematical computations at the console or the received signals may be attenuated using some other mechanism.

Each source structure and detector structure has a reference point. The reference points may be the centers of the sources and detectors if, for example, the sources and detectors have circular shapes. Alternatively, the reference point may be defined as some other point, so long as the definition is consistent among the sources and detectors. A line 725 that is parallel to an x-axis 750a passes through the reference point of each source structure.

A line 735 that is parallel to x-axis 750a passes through a reference point of detector structures 730a and 730b. A line 740 that is parallel to x-axis 750a passes through a reference point of detector structures 730c and 730d.

In the described embodiment, a distance y1 between line 725 and line 735 and along y-axis 750b describes a near-distance for the source and detector separation. A distance y4 between line 725 and line 740 and along y-axis 750b describes a far-distance for the source and detector separation. The near-distance y1 is different from the far-distance y4. Generally, y4 has a greater length than y1.

It should be appreciated that distance y1 and distance y4 may vary widely depending upon any number of factors. These factors include, but are not limited to, the number of source and detector structures, the overall size of the source and detector structures, the depth of tissue below the skin surface to be measured, and the application for which the sensor unit is intended. In general, y1 is approximately 30 millimeters. The difference between y1 and y4, i.e., y2, is approximately 10 millimeters. This then results in a distance y4 of approximately 40 millimeters.

In a specific implementation, the distance y2 between the detector structures will be less than the distance y1 or y4 between the source structures and detector structures. For example, if the distance between the detector structures is d then a distance from a source structure to a detector structure will be greater than d. However, in other implementations, the distance between the detector structures will be greater than a distance from a source structure to a detector structure.

A line 705 that is parallel to y-axis 750b passes through a reference point of source structures 715a, and detector structures 730a and 730c. A line 710 that is parallel to y-axis 750b passes through a reference point of source structure 715b, and detector structures 730b and 730d.

In the described embodiment, a distance x2 between line 705 and line 710 and along x-axis 750a is approximately 10 millimeters. It should be appreciated that distance x2 may vary widely depending upon any number of factors. These factors include, but are not limited to, the number of source and detector structures, the overall size of the source and detector structures, the depth of tissue below the skin surface to be measured, and the application for which the sensor unit is intended. For example, in another implementation, x2 may be 5 millimeters.

A distance x1 along x-axis 750*a* is between a side edge of the sensor housing base and line 750. A distance x3 along x-axis 750*a* is between an opposite side edge of the sensor housing base and line 710. These two distances describe how far from an edge of the sensor housing the source and detector structures are offset along the x-axis. In an implementation, x1 is the same as x3. However, in another implementation x1 is different from x3.

A distance y3 along y-axis 750*b* is between a top edge of the sensor housing base and line 725. A distance y5 along y-axis 750*b* is between a bottom edge of the sensor housing base and line 740. These two distances describe how far from an edge of the sensor housing the source and detectors are offset along the y-axis. In an implementation, y3 is different from y5. Y3 may be greater or less than y5. In another implementation, y3 and y5 may be the same.

A distance x4 and a distance y6 as shown in FIG. 7*a* describes the width and length, respectively, of the sensor housing base. In an implementation, x4 is approximately 42 millimeters and y6 is approximately 70 millimeters.

Table A below shows several implementations for the dimensions discussed above.

TABLE A

| Dimension | First Implementation (millimeters) | Second Implementation (millimeters) |
| --- | --- | --- |
| x1 | 11 | 7.7-14.3 |
| x2 | 10 | 7-13 |
| x3 | 11 | 7.7-14.3 |
| x4 | 32 | 29.4-54.6 |
| y1 | 30 | 21-39 |
| y2 | 10 | 7-13 |
| y3 | 11 | 7.7-14.3 |
| y4 | 40 | 28-52 |
| y5 | 22 | 15.4-28.6 |
| y6 | 73 | 49-91 |

In a specific implementation, the bottom surface area of the sensor base is greater than the combined areas of the openings for the source and detector structures. The area of the sensor base may be about 4 to 7 times greater than the combined areas of the openings. For example, it may be 4, 4.1, 4.3, 4.5, 4.7, 4.9, 5, 5.1, 5.2, 5.3, 5.4, 5.5, 5.6, 5.7, 5.8, 5.9, 6, 6.1, 6.3, 6.5, 6.7, 6.9, or more than 7 times greater than the combined areas of the openings. Depending on the specific application, the bottom surface area of the sensor base may be less than 4 times greater than the combined areas of the openings.

Adhesive film 760 allows the sensor housing to adhere to the tissue being monitored. Thus, it may be flexible and elastic so that it can conform to the surface of the tissue. In an implementation, the adhesive film is nonirritating to the human skin. A user can remove the sensor housing without leaving any residue or causing any damage to the patient's skin. In a specific implementation, the adhesive film may also be impregnated with antibiotics. This aids in preventing infections to sensitive skin.

In a specific embodiment, the adhesive film is matte finish, 3 mil transparent polyethylene, coated with a hypoallergenic, pressure sensitive acrylate adhesive. In other embodiments, the film is thicker or thinner, opaque or nontranslucent, or includes an alternative adhesive material (e.g., latex or silicone-based). The adhesive film may be a coating. The coating may be deposited using a brush or spray. The coating may be deposited as a series of small dots or lines. It may cover the entire bottom base of the sensor housing, or it may only cover a portion of the bottom base.

The adhesive film has openings. These openings match openings 720*a*, 720*b*, and 745 on the sensor housing base. The adhesive film is roughly rectangular in shape with rounded corners. The shape of the adhesive film typically matches the shape of the sensor housing base. However, in a specific implementation the adhesive film may extend past an edge or multiple edges of the sensor housing base. In another implementation, the adhesive film may not extend to an edge or multiple edges of the sensor housing base. This implementation allows a user to remove the sensor housing from the patient by grasping an unsecured edge of the sensor housing base to peel it away from the patient's tissue.

A release liner 765 with a pull-tab 770 is coupled to the adhesive film. The pull-tab is positioned at an edge adjacent to cable 746. The user removes the release liner to expose the adhesive film prior to adhering the sensor housing on the patient's skin. The release liner, in a specific embodiment, is a silicone treated, polyethylene coated, bleached kraft paper. In other embodiments, the liner is made of other materials such as claycoated paper, polycoated paper, polyester, or polypropylene, amongst others. It may be treated with a material such as silicone to allow for easy removal from the adhesive film.

In a specific embodiment, the release liner is a single piece with a pull-tab to allow removal of the liner from the adhesive film in one piece. In this embodiment, the pull-tab is generally at the edge of the release liner closest to the cable. However, the pull-tab can be on other edges of the release liner. In another specific embodiment, the release liner is in multiple sections. For example, the release liner may be trisected to allow removal of the release liner in stages. Other embodiments could include fewer or more sections of liner, with or without pull-tabs. In lieu of or in addition to a pull-tab, the liner may be split to aid in removal of the liner from the adhesive film.

In a specific implementation, the four detectors are positioned at the vertices of a square; however, the detectors may be positioned at vertices of any quadrilateral. The sources are arranged linearly and symmetrically distanced from the detectors.

In a symmetrical arrangement, the sensors are arranged so there is a first distance between a first detector and a first source and a second distance between the first detector and a second source, where the first and second distances are equal. In another example, the sensor openings are arranged so there is a first distance between a first source and a first detector and a second distance between the first source and a second detector, where the first and second distances are equal.

In another symmetrical arrangement, the sensors are arranged so there is a first distance between a first source and a first detector. There is a second distance between the first source and a second detector. There is a third distance between a second source and the first detector. There is a fourth distance between the second source and the second detector. The arrangement is symmetrical the first distance is equal to the fourth distance, and the second distance is equal to the third distance.

In another implementation, the arrangement of sources and detectors is asymmetrical. An asymmetrical arrangement of sources and detectors is discussed in U.S. Pat. No. 7,355,688, which is incorporated by reference. Any of the asymmetrical arrangements of sources and detectors discussed in that patent is applicable to the sources and detectors in this application.

Figure 7B:
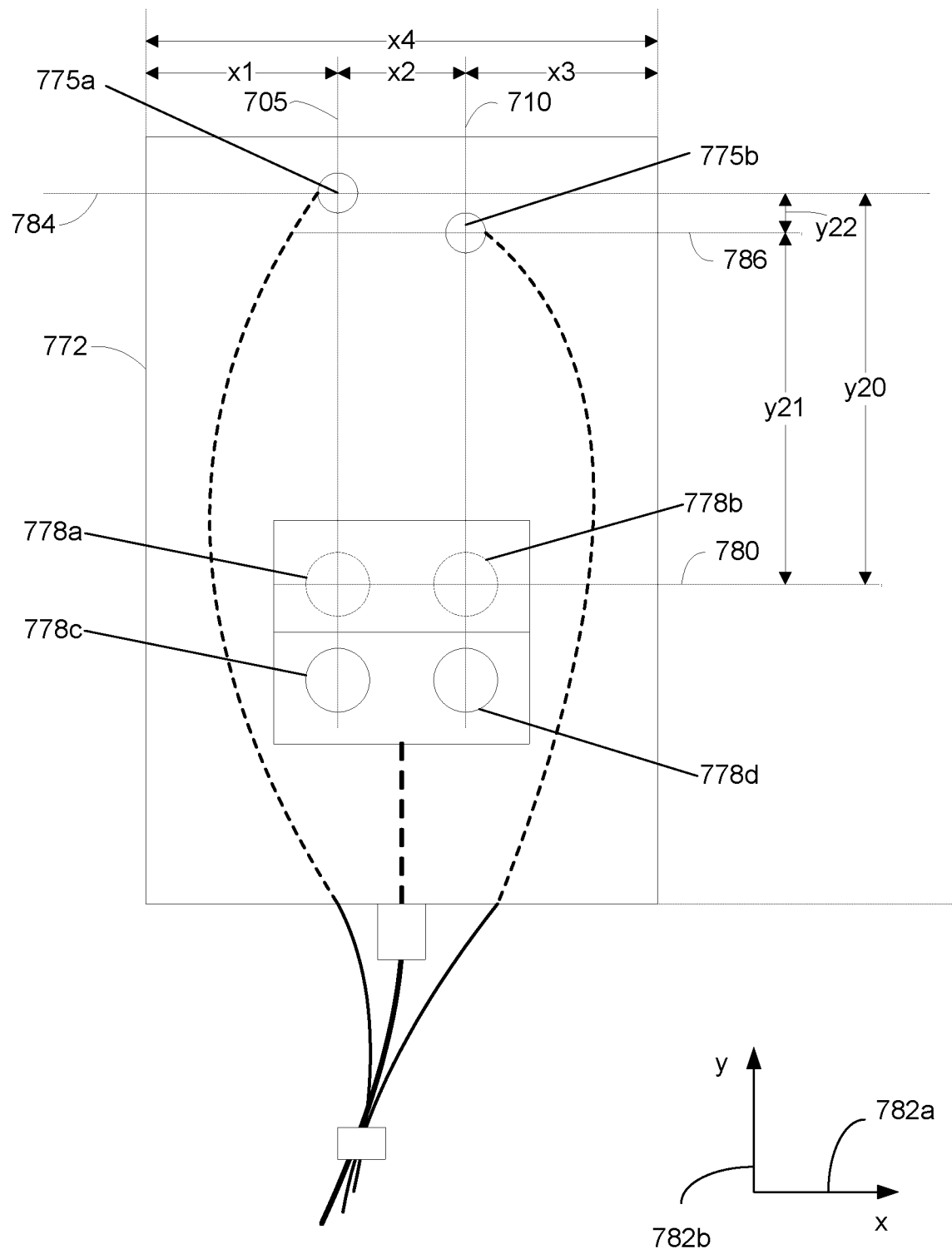
FIG. 7b shows a bottom view of an implementation of an asymmetrical sensor.

FIG. 7b shows an example of an asymmetrical arrangement of sensors. A sensor head 772 includes sources 775a and 775b and detectors 778a, 778b, 778c, and 778d. Sources 775a and 775b are arranged such that they are in an offset arrangement relative to detectors 778a, 778b, 778c, and 778d. That is, source 775a and 775b are not equidistant to detectors 778a, 778b, 778c, and 778d relative to at least one axis. Detectors 778a and 778b are arranged such that a line 780 of detectors 778a and 778b is approximately parallel to an x-axis 782a. Typically, line 780 passes through a reference point of each detector 778a and 778b. Sources 775a and 775b are arranged such that a line 784 of source 775a is parallel to a line 786 of source 775b, but is not coincident with line 784. Line 784 passes through a reference point of source 775a and is parallel to x-axis 782a, while line 786 passes through a reference point of source 775b and is parallel to x-axis 782a.

A distance y20 between line 784 and line 780 along a y-axis 782b differs from a distance y21 between line 786 and line 780. Although distance y20 is shown as being greater than distance y21, it should be appreciated that distance y21 may instead be greater than y20. The difference between distance y20 and distance y21 is generally characteristic of the offset arrangement, or substantially unbalanced arrangement, of sources 775a and 775b relative to detectors 778a and 778b. In other words, there is effectively a lack of symmetry in the placement of sources 775a and 775b.

Distance y20 may be approximately 34 millimeters, while distance y21 may be approximately 30 millimeters. It should be appreciated that distance y20 and distance y21 may vary widely depending upon any number of factors. The factors include, but are not limited to, the overall size of the sources and detectors, the overall size of the sensor head, and the application for which sensor head 772 is intended. In general, the difference between distance y20 and distance y21 (i.e., y22) ranges from about 3 to 5 millimeters. For example, y22 may be 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or more than 5 millimeters. In other implementations, y22 may be less than 3 millimeters.

As a further example, in an asymmetrical arrangement, the sensors are arranged so there is a first distance between a first detector and a first source and a second distance between the first detector and a second source, where the first and second distances are not equal. In another example, the sensor openings are arranged so there is a first distance between a first source and a first detector and a second distance between the first source and a second detector, where the first and second distances are not equal.

In another asymmetrical arrangement, the sensors are arranged so there is a first distance between a first source and a first detector. There is a second distance between the first source and a second detector. There is a third distance between a second source and the first detector. There is a fourth distance between the second source and the second detector. The arrangement is asymmetrical when the first distance is not equal to the fourth distance, and the second distance is not equal to the third distance.

In other implementations, two or more sensor probes of the invention may be used. Multiple sensors may be useful when, for example, multiple tissue oxygen saturation readings are desired at different regions. When using two probe pads, there will be a total of four sources and eight detectors. These probe pads may be placed on different sides of a patient's head. An advantage of using greater number of sources and detectors is to allow for taking more detailed and accurate measurements.

Even greater number of pads (more than two) may be used, but there is typically a limited amount of surface area on a person's head in which to place the pads. Therefore, there is an advantage to having greater numbers of sources and detectors for a single pad.

When multiple sensor probe pads are used, each pad may have a symmetrical or asymmetrical arrangement of sources and detectors as discussed above.

Figure 8:
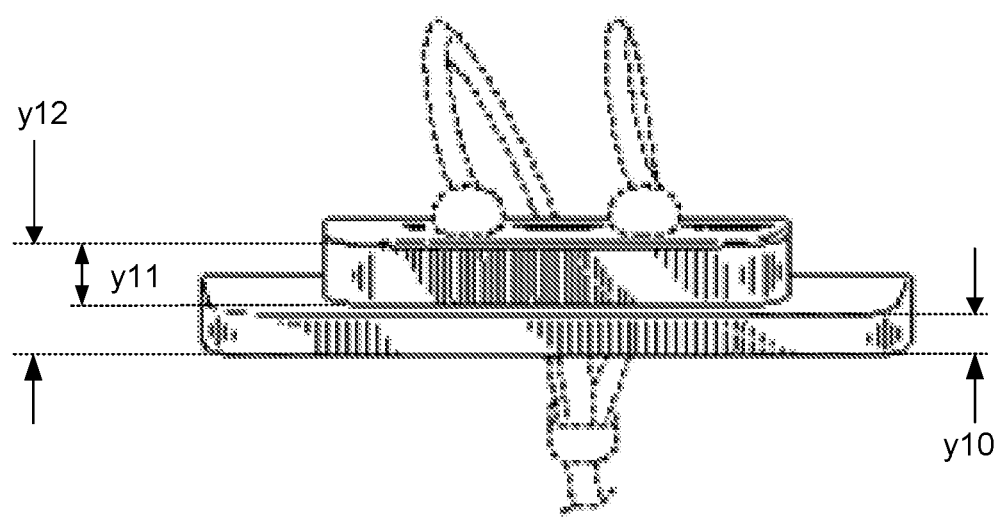
FIG. 8 shows a front view of the sensor.

FIG. 8 shows a front view of the sensor with dimensions to indicate the thickness of the various parts of the sensor. A distance y10 represents the thickness of the base. A distance y11 represents the thickness of the detector and source housings. A distance y12 represents the total thickness of the sensor housing.

In a specific implementation, the detector and source housings are thicker than the base. Placing the thicker detector and source housings on opposite sides of the thinner base as shown in previous figures helps to ensure the flexibility of the sensor as the detector and source housings can rotate towards each other. At the same time, the thicker detector and source housings can properly support the embedded detector structures and source structures. The entire surface area of the base can then fully contact the tissue to create a dark environment. An overly thick base presents problems. Source light may escape and ambient light may enter when such a base is placed on a curved surface. Due to the thickness, such a base may not have sufficient flexibility to completely contact the surface. Instead, a crease may form which lets source light escape and ambient light in. This could then result in inaccurate readings.

The exact thickness of the source and detector housings and base will vary with the size of the embedded source and detector structures. As noted, typically, source and detector housings will be thicker than the thickness of the base. For example, if the thickness of an uncompressed source or detector housing is x, then the thickness of the uncompressed base should be less than x.

In a specific implementation, the detector and source housings may include several layers of cushioning material such as polyethylene foam in order to properly support the source and detector structures. For example, the detector and source housings may be made with 2, 3, 4, 5, or more layers of 3.18 millimeter thick polyethylene foam. In an implementation, the thickness of the detector and source housing is approximately three times the thickness of the base. For example, the housings may be two, four, five, or more than five times as thick as the base. Table B below shows several implementations for the thickness of the sensor housing.

TABLE B

| Dimension | First Implementation (millimeters) | Second Implementation (millimeters) |
|---|---|---|
| y10 | 3.18 | 2.2-4.1 |
| y11 | 9.54 | 6.7-12.4 |
| y12 | 12.72 | 8.9-16.5 |

Figure 9:
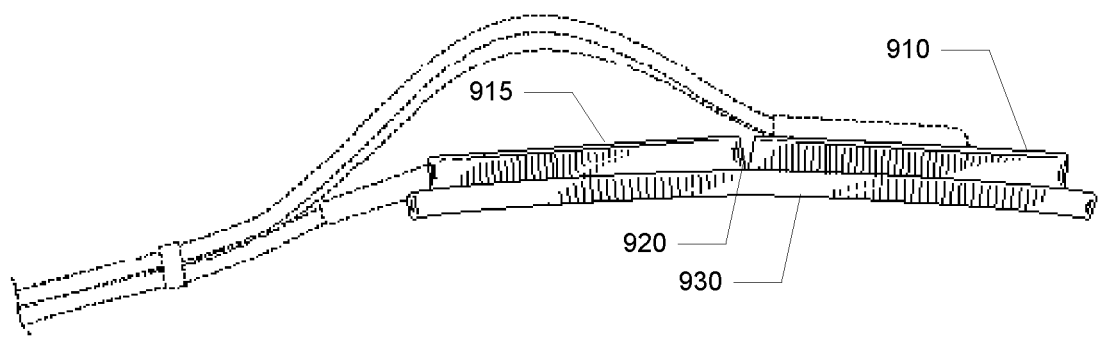
FIG. 9 shows a side view of the sensor.

FIG. 9 shows a side view of the sensor. Source housing 910 and detector housing 915 curve about a separation 920. This produces a curve in a base 930. This allows the base to conform more easily to curved surfaces, such as the curved surface of a patient's skin.

Figure 10:
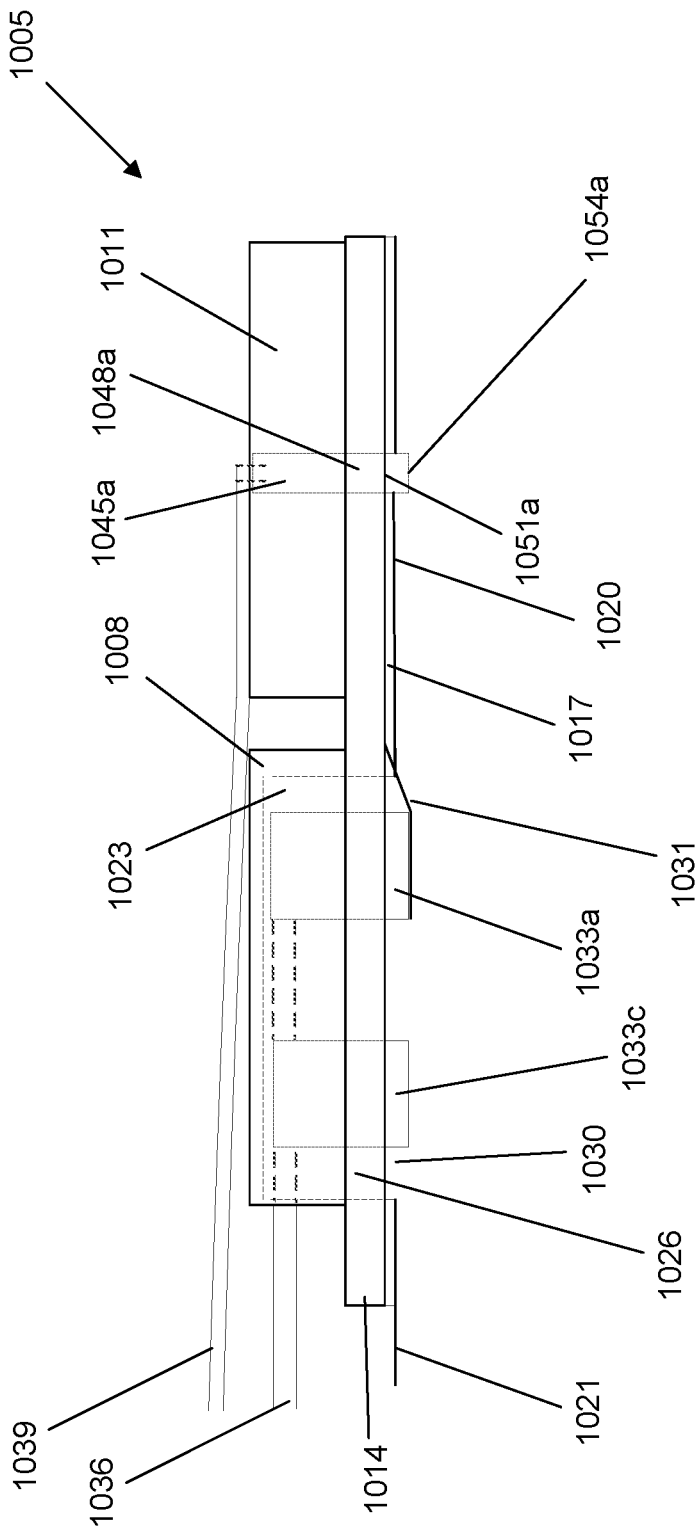
FIG. 10 shows a cross-sectional view of the sensor.

FIG. 10 shows a cross-sectional view of the sensor. The sensor includes a sensor housing 1005 which in turn includes a detector housing 1008, a source housing 1011, and a base 1014. An adhesive film 1017 covers the bottom surface of the sensor housing base. A release liner 1020 with a pull-tab 1021 covers the adhesive film.

Detector housing 1008 includes a cavity 1023. Cavity 1023 opens into a cavity 1026 in the base. Cavity 1026 is coupled to opening 1030 on the bottom surface of the base which is partially covered by a light diffusing layer or semitranslucent film 1031. Cavities 1023 and 1026 hold detectors 1033a, 1033b (not shown in this view), 1033c, and 1033d (not shown in this view). An adhesive may be used to secure the detectors in the cavity.

In a specific implementation with, for example, smaller detector structures, the detector structures may not extend into cavity 1023. Thus, cavity 1023 may only contain cable 1036. In another implementation, the detector structures may have an even smaller profile such that they only occupy a portion of cavity 1026. In this case, cable 1036 may also extend into cavity 1026 to connect with the detector structures.

Cables 1039 and 1042 (not shown in this view) enter into cavities in the source housing. Cable 1039 enters into a cavity 1045a in the source housing. Cavity 1045a opens into a cavity 1048a in the base. Cavity 1048a is coupled to opening 1051a. Cavities 1045a and 1048a hold source structure 1054a. An adhesive may be used to secure the source structure in the cavities.

Though not shown in this view, a cable 1042 similarly enters cavities in the source housing and base.

In a specific implementation, cables 1039 and 1042 travel along the top surface of the source housing to approximately the midpoint of the source housing before entering into their respective cavities. This provides for a more secure connection of the cables to the source housing. However, in other implementations, the cables will not travel along the top surface of the source housing and will directly enter the cavity. In another implementation, the cables will travel along the top surface of the sensor housing and enter the cavity before reaching the midpoint of the sensor housing. In yet another implementation, the cables will travel past the midpoint of the sensor housing before entering the cavity. In still another implementation, the cables will also travel along the top surface of the detector housing.

In a specific implementation, the bottom surface of the detector and source structures is in the same plane as the bottom surface of base. In other implementations, the detector and source structures will extend past the bottom surface of the base, release liner, or both. The detector and source structures may extend past the bottom surface of the base from about 0.5 millimeters to about 1.5 millimeters. For example, the bottom surface of the detector and source structures may extend about 0.6, 0.7, 0.8, 0.9, 1.0, 1.1, 1.2, 1.3, 1.4, 1.5 millimeters or more past the bottom surface of the base. This helps to ensure, for example, good contact of the detector and source structures to with the tissue.

In yet another implementation, the detector and source structures may be recessed into the bottom surface of the base. The detector and source structures may be recessed from about 0.1 to 1.0 millimeters. For example, the bottom surface of the detector and source structures may be recessed about 0.2, 0.3, 0.4, 0.5, 0.6, 0.7, 0.8, 0.9 millimeters, or more into the base.

In a specific implementation, the release liner covers the openings for the detector and source structures. This helps to protect the detector and source structures from debris. In other implementations, there may be openings in the release liner that match the openings in the base for the detector and source structures.

Figure 11C:
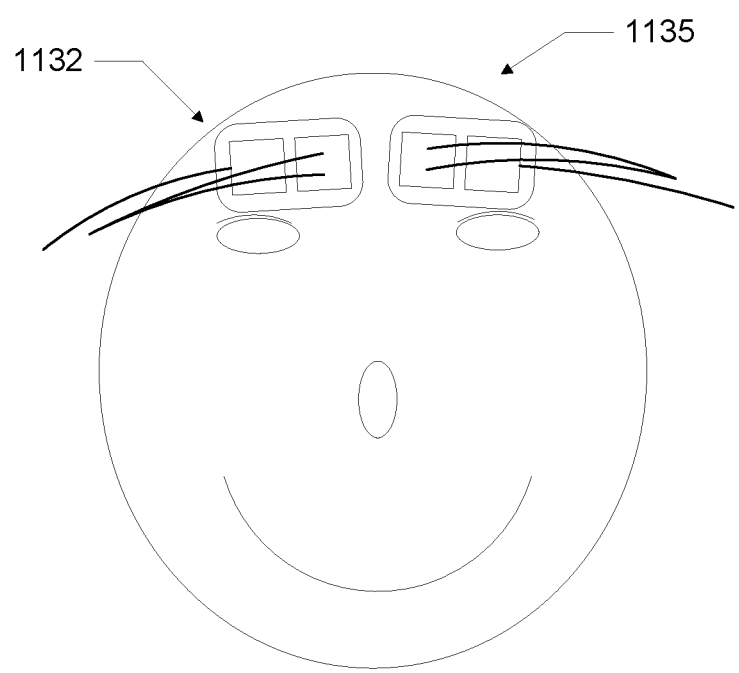
FIG. 11c shows two sensors simultaneously placed on the right and left sides of a patient's forehead.

FIGS. 11a-11c show various placements of the sensor on the patient's forehead.

FIG. 11a shows a first implementation of a sensor 1105 placed on a right side 1108 of a patient's forehead 1111. The sensor includes an edge 1114 and an inferior border 1117. In an implementation, the sensor is placed with the inferior border approximately 1 centimeter above a patient's eyebrow 1120 and with edge 1114 approximately 1 centimeter away from a midline 1123 of the patient's forehead.

FIG. 11b shows a second implementation of a sensor 1126 placed on a left side 1129 of the patient's forehead. In an implementation, a left-hand side placement of the sensor is a mirror image of the right-hand side placement.

FIG. 11c shows a third implementation where sensors 1132 and 1135 are concurrently placed on left and right sides of a patient's forehead. In a specific implementation, each sensor calculates an oxygen saturation measurement independent of the other sensor. This allows, for example, a baseline measurement of one side to be made which can then be compared with a measurement of the other side.

In a specific implementation, the invention measures cerebral tissue oxygen saturation. This measurement can be used to assess oxygen supply and blood circulation in the brain for the purpose of guiding cardiac surgeries or other types of surgeries that would affect oxygen supply and blood circulation in the brain. The different sensor placements allow measurements to be taken at different regions of the brain. Different regions of the brain control may control different functions. Thus the measurements are useful in, for example, diagnosis and monitoring. For example, the left side of the brain typically controls language and speech skills. The right side of the brain typically controls spatial perception and orientation.

Figure 12:
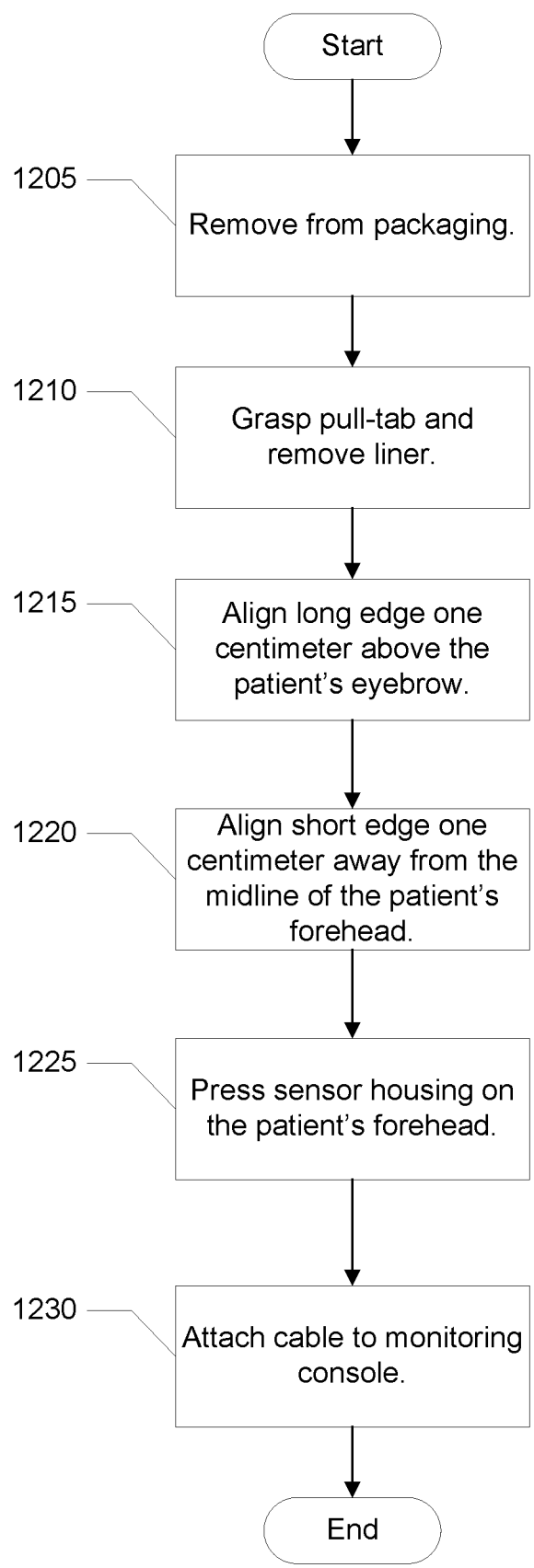
FIG. 12 shows a process flow for using the system.

FIG. 12 shows a process flow for using the sensor in accordance with an embodiment of the present invention. No threshold readings are required prior to taking a measurement.

In a step 1205, the user removes the sensor and its attached cables from a sterile package. In a step 1210, the user removes the release liner by grasping the cable with one hand and pulling on the pull-tab with the other hand. This exposes the adhesive. In a specific implementation, a multipiece release liner may be used in lieu of or in addition to a pull-tab.

The user can place the sensor on the patient's left forehead, right forehead, or both the left and right forehead. In a step 1215, the user aligns a long edge (i.e., inferior border from FIG. 11a) of the sensor approximately one centimeter above the patient's eyebrow. In a step 1220, the user aligns a short edge of the sensor approximately one centimeter away from the midline of the patient's forehead.

In a step 1225, the user presses the sensor onto the patient's forehead. This secures the sensor to the patient's skin. In a step 1230, the user then attaches the cables to the monitoring consol.

Figure 13:
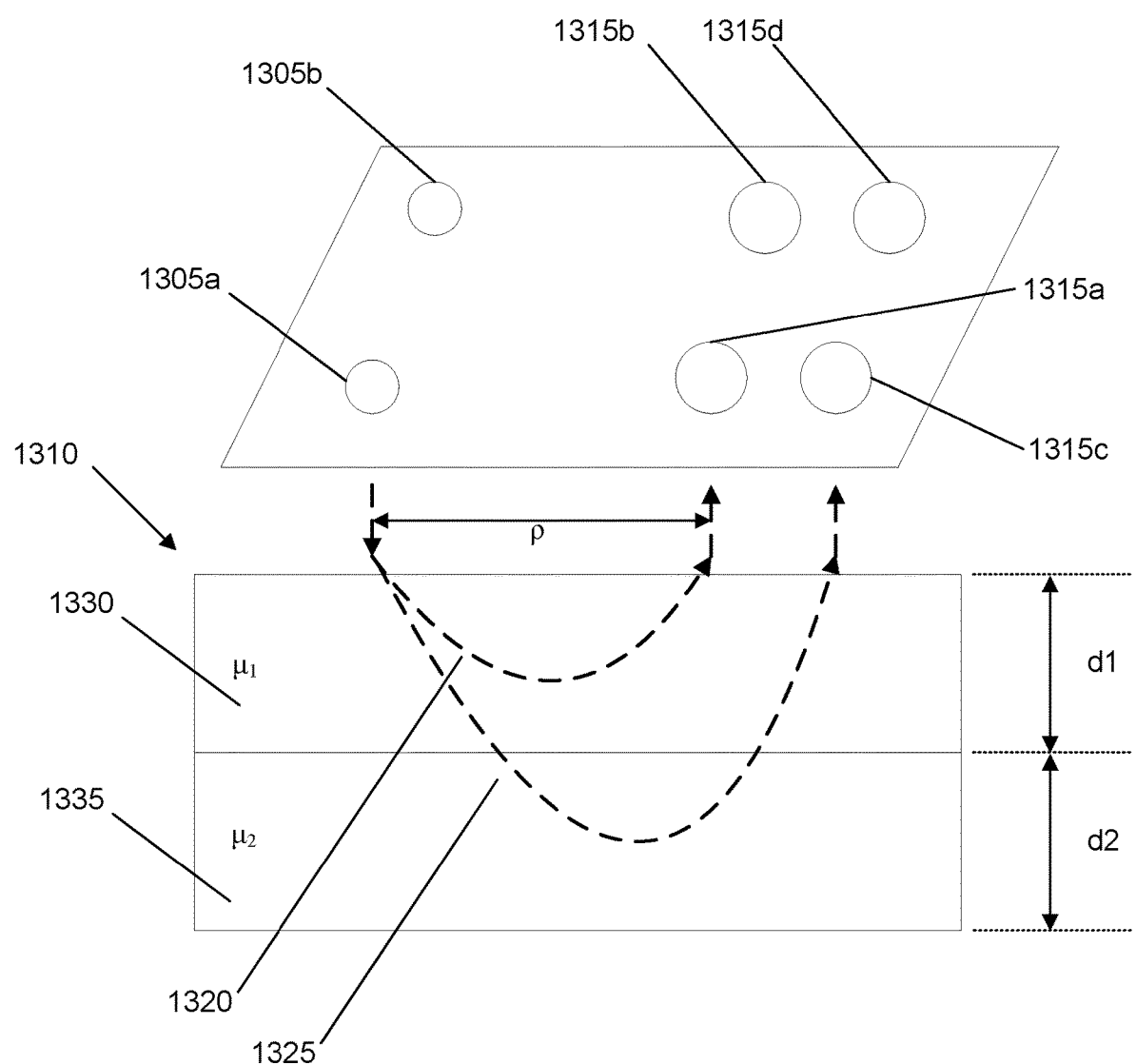
FIG. 13 shows a schematic diagram of the sensor in use.

FIG. 13 is a schematic diagram of the sensor unit in use. The sensor unit includes source structures 1305a and 1305b which transmit light into a human head 1310 and detector structures 1315a, 1315b, 1315c, 1315d which receive the transmitted light. Optical paths 1320, 1325 of the light generally follows the shape of a banana. The human head is modeled as a medium with two layers—a shallow layer 1330 and a deep layer 1335.

The shallow layer includes the scalp, skull, and cerebrospinal fluid. The attenuation coefficient for the shallow layer is $\mu_1$. The thickness d1 of the shallow layer is generally 12 millimeters.

The deep layer is the brain including gray matter and white matter. The attenuation coefficient for the shallow layer is $\mu_2$. The thickness d2 of the deep layer is considered infinite.

Table C below summarizes several optical properties of the adult head at a near infrared wavelength of 800 nanometers.

TABLE C

| Tissue Type | Thickness (millimeters) | Scattering Coefficient $\mu$'s (1/millimeter) | Absorption Coefficient $\mu_a$ (1/millimeter) |
|---|---|---|---|
| Scalp and skull | 10 | 2.0 | 0.04 |
| Cerebrospinal fluid | 2 | 0.01 | 0.001 |
| Gray matter | 4 | 2.5 | 0.025 |
| White matter | ∞ | 6.0 | 0.005 |

In an implementation having a symmetrical source and detector arrangement as discussed in FIG. 7a, a distance between the source and detectors is p. In an implementation having a nonsymmetrical or asymmetrical source and detector arrangement as discussed in FIG. 7b, there may be two different distances between sources and detectors such as p and p plus an offset distance that typically ranges from about 3 to 5 millimeters.

This represents the separation between the position where light enters the medium and the position where light exits from the medium. In an implementation, as described earlier, a near distance between the source and detectors is 30 millimeters. A far distance between the source and detectors is 40 millimeters. Sources transmit light into the shallow and deep layers. Detectors detect any resultant light that exits the shallow and deep layers.

In a specific implementation, a single pulse of light is transmitted into the tissue. The light is then received by the near detectors (i.e., 1315a and 1315b) and far detectors (i.e., 1315c and 1315d). A first attenuation value is then determined based on the light received by the near detectors. This first attenuation value is used to calculate an attenuation coefficient for the shallow layer. The attenuation coefficient of the deep layer is then calculated by using the shallow layer attenuation coefficient and a second attenuation value based on light received by the far detectors. The tissue oxygen saturation of the deep layer is then calculated.

In another implementation, multiple pulses of light such as two pulses of light are transmitted into the tissue. A first pulse of light may be received by the near detectors and a first attenuation value determined. A second pulse of light may be received by the far detectors and a second attenuation value determined. The first attenuation value may be used to calculate an attenuation coefficient for the shallow layer. The attenuation coefficient of the deep layer may then be calculated by using the shallow layer attenuation coefficient and the second attenuation value. The tissue oxygen saturation of the deep layer may then be calculated.

A Monte Carlo simulation can be used to describe the photon propagation. For example, let $\gamma(\rho)$ be the light intensity profile, where $\gamma(\rho)\,\delta\rho$ can be interpreted as the probability that a photon exits the surface at a distance between $\rho$ and $\rho+\delta\rho$. The intensity profile can be represented by the following equation:

$$\Gamma(\rho) \approx \frac{1}{4\pi\rho^2}\left[\sqrt{6\mu_1}\, e^{-\rho\sqrt{6\mu_1}} + \sqrt{6\mu_2}\, e^{-\rho\sqrt{6\mu_2}\, -m(\mu_1-\mu_2)}\right], \mu_1 > \mu_2 \quad (1)$$

$$\text{where } m = \frac{5.2d1}{\sqrt{\mu_1}}.$$

According to table C, d1=1.2 centimeters, i.e., 12 millimeters.

For the shallow layer, $\mu_1 = \mu_2$ $$\Gamma(\rho) \approx \frac{1}{2\pi\rho^2}\sqrt{6\mu_1}\, e^{-\rho\sqrt{6\mu_1}}$$

In the auto-calibration scheme, $$\Gamma^{(4)} \approx \left(\frac{\rho_{12}\rho_{21}}{\rho_{11}\rho_{22}}\right)^2 e^{-(\rho_{11}-\rho_{12}+\rho_{22}-\rho_{21})\sqrt{6\mu_1}}, \quad (2)$$

Therefore, $$\mu_1 = \frac{1}{6}\left[\frac{2\ln\frac{\rho_{12}\rho_{21}}{\rho_{11}\rho_{22}} - \ln\Gamma^{(4)}}{\rho_{11}-\rho_{12}+\rho_{22}-\rho_{21}}\right]^2$$

The attenuation coefficient for deep layer $\mu_2$ is then determined using equation 1 using the attenuation coefficient for the shallow layer $\mu_1$ calculated from equation 2.

The generalized governing equation for describing migration of photons or propagation of electromagnetic waves in a medium is given by:

$$I = \alpha\cdot\beta\cdot\gamma\cdot I_o\cdot e^{(-\beta\cdot L\cdot\delta\cdot\Sigma_i(\epsilon_i C_i)+\sigma)} \quad (3)$$

It is appreciated that the system parameters "γ" and "δ" may have the value of 1.0 and "σ" may be 0.0. One simplified version of equation 3 may be obtained when the parameters "γ" and "δ" are approximated as a unity:

$$I = \alpha\cdot\beta\cdot I_o\cdot e^{(-\beta\cdot L\cdot\rho_i(\epsilon_i\cdot C_i)+\sigma)} \quad (4)$$

The convention "photon diffusion equation" has the same form as equation 4:

$$I = S\cdot D\cdot I_o\cdot e^{(-\beta\cdot L\cdot\Sigma_i(\epsilon_i\cdot C_i)+A)} \quad (5)$$

where "S" corresponds to "a" of equation 4 and generally accounts for characteristics of the wave source such as power and configuration thereof, mode of optical coupling between the wave source and medium, or optical coupling loss therebetween, and combinations of these, "D" corresponds to "β" of equation 4 and generally accounts for characteristics of the wave detector, mode of optical coupling between the wave detector and medium, or the associated coupling loss, and combinations of these, and "A" corresponds to "δ" of equation 4 which may be either a proportionality constant or a parameter associated with the wave source, wave detector, or medium, and combinations of these.

For illustration purposes, an exemplary optical system may include, e.g., two wave sources (S1 and S2) each emitting electromagnetic waves of wavelength $\lambda_1$ and two wave detectors (D1 and D2) arranged to detect at least a portion of such electromagnetic waves. Applying the photon diffusion equation 5 to each pair of the wave sources and detectors of the exemplary optical system yields the following set of equations:

$$I_{S1D1}^{\lambda 1} = I_{S1}^{\lambda 1} \cdot S_1 \cdot D_1 \cdot e^{-B_{S1D1}(\rho_j \varepsilon_j^{\lambda 1} C_j) L_{S1D1} + A} \quad (6)$$

$$I_{S1D2}^{\lambda 1} = I_{S1}^{\lambda 1} \cdot S_1 \cdot D_2 \cdot e^{-B_{S1D2}(\rho_j \varepsilon_j^{\lambda 1} C_j) L_{S1D2} + A} \quad (7)$$

$$I_{S2D1}^{\lambda 1} = I_{S2}^{\lambda 1} \cdot S_2 \cdot D_1 \cdot e^{-B_{S2D1}(\Sigma_j \varepsilon_j^{\lambda 1} C_j) L_{S2D1} + A} \quad (8)$$

$$I_{S2D2}^{\lambda 1} = I_{S2}^{\lambda 1} \cdot S_2 \cdot D_2 \cdot e^{-B_{S2D2}(\Sigma_j \varepsilon_j^{\lambda 1} C_j) L_{S2D2} + A} \quad (9)$$

where the superscript $\lambda_1$ denotes that various variables and parameters are obtained at the wavelength of $\lambda_1$.

A mathematical operation may eliminate at least one system parameter from the equations 6 to 9. For example, the source coupling factors such as $S_1$ and $S_2$ may be canceled therefrom by taking the first ratio of the equation 6 to 7 and by taking the fourth ratio of the equation 8 to 9. Logarithms of the first and second ratios are then taken to yield what are conventionally termed as "optical densities" (i.e., $OD_1^{\lambda 1}$ is defined as a logarithm of $I_{S1D1}^{\lambda 1}/I_{S1D2}^{\lambda 1}$ and $OD_2^{\lambda 2}$ defined as a logarithm of $I_{S2D2}^{\lambda 1}/I_{S2D1}^{\lambda 1}$). It is noted that these optical densities are generally insensitive to exact modes of optical coupling between the wave source and the physiological medium:

$$OD_1^{\lambda_1} = \ln\frac{I_{S1D1}^{\lambda_1}}{I_{S1D2}^{\lambda_1}} = \ln\frac{D_1}{D_2} + \left(B_{S1D2}^{\lambda_1} L_{S1D2} - B_{S1D1}^{\lambda_1} L_{S1D1}\right) \sum_i \varepsilon_i^{\lambda_1} C_i \quad (10)$$

$$OD_2^{\lambda_1} = \ln\frac{I_{S2D2}^{\lambda_1}}{I_{S2D1}^{\lambda_1}} = \ln\frac{D_2}{D_1} + \left(B_{S2D1}^{\lambda_1} L_{S2D1} - B_{S2D2}^{\lambda_1} L_{S2D2}\right) \sum_i \varepsilon_i^{\lambda_1} C_i \quad (11)$$

$$OD^{\lambda_1} = OD_1^{\lambda_1} + OD_2^{\lambda_1} \quad (12)$$

The cerebral tissue oxygen saturation can then be calculated using, in part, equations 10 and 11, or equation 12, i.e., an automatic error cancellation scheme. These equations are discussed in more detail as equations 5a and 5b in U.S. Pat. No. 6,597,931, which is incorporated by reference.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A method comprising:
    positioning a sensor head of an oximeter to face toward a tissue, wherein the sensor head comprises a first source structure, a second source structure, a far detector arrangement, and a near detector arrangement;
    transmitting light through the first source structure and the second source structure into a tissue:
    receiving a first light transmitted through the tissue at the near detector arrangement;
    receiving a second light transmitted through the tissue at the far detector arrangement; and
    processing the first and second received light using an electronic processor,
    wherein a semitranslucent film covers the near detector arrangement, and the first received light has passed through the semitranslucent film while the second received light has not passed through the semitranslucent film.

2. The method of claim 1 wherein the oximeter measures oxygen saturation of the tissue without requiring a pulse.

3. The method of claim 1 wherein the first received light comprises an attenuation characteristic due to, at least in part, having been passed through the semitranslucent film.

4. A method comprising:
    providing a sensor head of a medical device, wherein the sensor head is configured to be placed adjacent to a tissue;
    forming a first source structure on a tissue contacting side of the sensor head;
    forming a first near detector structure on the tissue contacting side of the sensor head;
    forming a first far detector structure on the tissue contacting side of the sensor head; and
    positioning a light diffusing layer to overlay the first near detector structure and not overlay the first far detector structure.

5. The method of claim 4 wherein the first near detector structure receives a beam of light after the beam of light has been transmitted through the tissue and the light diffusing layer, and the first far detector structure receives the beam of light without the beam of light being transmitted through the light diffusing layer.

6. The method of claim 4 comprising:
    arranging the first source structure, first near detector structure, and first far detector structure in a line.

7. The method of claim 4 wherein a first distance between the first source structure and the first near detector structure is different from a second distance between the first source structure and first far detector structure.

8. The method of claim 7 wherein the first distance is less than the second distance.

9. The method of claim 7 wherein the first distance is approximately 30 millimeters.

10. The method of claim 7 wherein the second distance is approximately 40 millimeters.

11. The method of claim 4 comprising:
    forming a second source structure on the tissue contacting side of the sensor head;
    forming a second near detector structure on the tissue contacting side of the sensor head; and
    forming a second far detector structure on the tissue contacting side of the sensor head.

12. The method of claim 11 comprising:
    positioning a light diffusing layer to overlay the second near detector structure and not overlay the second far detector structure.

13. The method of claim 12 wherein the second near detector structure receives a beam of light after the beam of light has been transmitted through the tissue and the light diffusing layer.

14. The method of claim 11 comprising:
    arranging the second source structure, second near detector structure, and second far detector structure in a line.

15. The method of claim 11 wherein a third distance between the second source structure and the second near detector structure is different from a fourth distance between the second source structure and second far detector structure.

16. The method device of claim 11 wherein the third distance is less than the fourth distance.

17. The method for claim 4 wherein the medical device is an oximeter.

18. The method for claim 4 wherein the medical device is a tissue oximeter.

19. A method comprising:
providing a sensor head of a medical device;
forming a first source structure on a tissue contacting side of the sensor head;
forming a first near detector structure on the tissue contacting side of the sensor head;
forming a first far detector structure on the tissue contacting side of the sensor head; and
positioning a light diffusing layer to overlay the first near detector structure and not overlay the first far detector structure;
positioning the tissue contacting side of the sensor head against a tissue;
transmitting light through the first source structure into the tissue;
receiving a first light transmitted through the tissue at the near detector arrangement;
processing the first received light by way of an electronic processor.

20. The method of claim 19 wherein the first near detector structure receives a beam of light after the beam of light has been transmitted through the tissue and the light diffusing layer, and the first far detector structure receives the beam of light without the beam of light being transmitted through the light diffusing layer.

21. The method of claim 20 wherein the first received light comprises an attenuation characteristic due to, at least in part, having been passed through the semitranslucent film.

22. The method of claim 19 comprising:
arranging the first source structure, first near detector structure, and first far detector structure in a line.

23. The method of claim 19 wherein a first distance between the first source structure and the first near detector structure is different from a second distance between the first source structure and first far detector structure.

24. The method for claim 19 wherein the medical device is an oximeter.

25. The method for claim 19 wherein the medical device is a tissue oximeter.

* * * * *